(12) United States Patent
Chalberg, Jr.

(10) Patent No.: US 12,270,033 B2
(45) Date of Patent: Apr. 8, 2025

(54) DUAL LEUCINE ZIPPER KINASE INHIBITORS FOR GENE THERAPY

(71) Applicants: Exhaura, Ltd., Palo Alto, CA (US); Thomas W. Chalberg, Jr., Redwood City, CA (US)

(72) Inventor: Thomas W. Chalberg, Jr., Redwood City, CA (US)

(73) Assignee: Exhaura, Ltd., Palo Alto, CA (US)

( * ) Notice: Subject to any disclaimer, the term of this patent is extended or adjusted under 35 U.S.C. 154(b) by 750 days.

(21) Appl. No.: 17/430,269

(22) PCT Filed: Feb. 13, 2020

(86) PCT No.: PCT/US2020/018161
§ 371 (c)(1),
(2) Date: Aug. 11, 2021

(87) PCT Pub. No.: WO2020/168111
PCT Pub. Date: Aug. 20, 2020

(65) Prior Publication Data
US 2022/0213494 A1    Jul. 7, 2022

Related U.S. Application Data

(60) Provisional application No. 62/806,213, filed on Feb. 15, 2019, provisional application No. 62/806,210, filed on Feb. 15, 2019.

(51) Int. Cl.
*C12N 9/12* (2006.01)
*C12N 15/79* (2006.01)

(52) U.S. Cl.
CPC ............... *C12N 15/79* (2013.01); *C12N 9/12* (2013.01); *C12N 2750/14143* (2013.01); *C12Y 207/11025* (2013.01)

(58) Field of Classification Search
CPC ................. C12N 15/79; C12N 9/12; C12N 2750/14143; C12Y 207/11025
See application file for complete search history.

(56) References Cited

U.S. PATENT DOCUMENTS 9,101,645 B2    8/2015  Watts et al.
9,434,928 B2    9/2016  Mendell et al.
(Continued)

FOREIGN PATENT DOCUMENTS

EP    2295564 A1    3/2011
WO    WO95023849 A1    9/1995
(Continued)

OTHER PUBLICATIONS

Patel et al., J. Med. Chem. (2015) 58(1): 401-418 (Year: 2015).*
(Continued)

*Primary Examiner* — Evelyn Y Pyla
*Assistant Examiner* — Katherine R Small
(74) *Attorney, Agent, or Firm* — COOLEY LLP

(57) ABSTRACT

The disclosure provides compositions and methods useful for treating conditions related to Dual Leucine Zipper (DLK), e.g., neurodegenerative disorders including optic neuropathy. The disclosure provides gene constructs and vectors that regulate the activity of Dual Leucine Zipper Kinase (DLK) or Leucine Zipper Kinase (LZK). The disclosure also provides dominant negative DLK (DN-DLK) proteins that inhibit the kinase and/or signaling activity of DLK. The disclosure also provides vectors, pharmaceutical compositions, and methods of inhibiting DLK.

16 Claims, 13 Drawing Sheets
Specification includes a Sequence Listing.

(56) References Cited

U.S. PATENT DOCUMENTS

| | | | |
|---|---|---|---|
| 9,708,604 | B2 | 7/2017 | Collard et al. |
| 10,000,741 | B2 | 6/2018 | Chalberg et al. |
| 2012/0278912 | A1 | 11/2012 | Farrar |
| 2012/0328609 | A1* | 12/2012 | Lewcock ............... A61P 39/02 514/17.7 |
| 2014/0248701 | A1 | 9/2014 | Simpson et al. |
| 2015/0259395 | A1 | 9/2015 | Chalberg et al. |
| 2015/0376240 | A1 | 12/2015 | Cronin et al. |
| 2018/0066022 | A1 | 3/2018 | Chalberg et al. |
| 2018/0100165 | A1 | 4/2018 | Boye et al. |
| 2018/0258446 | A1 | 9/2018 | Park et al. |

FOREIGN PATENT DOCUMENTS

| | | |
|---|---|---|
| WO | WO0183692 A2 | 11/2001 |
| WO | WO02053703 A2 | 7/2002 |
| WO | WO2006108201 A1 | 10/2006 |
| WO | WO2011106783 A2 | 9/2011 |
| WO | WO2015054653 A2 | 4/2015 |
| WO | WO2018009562 A1 | 1/2018 |
| WO | WO2018013932 A1 | 1/2018 |
| WO | WO2019195765 A1 | 10/2019 |

OTHER PUBLICATIONS

Chen et al., The Journal of Neuroscience (2008) 28(3): 672-680 (Year: 2008).*

Extended European Search Report for Application No. 20754951.0, mailed Nov. 10, 2022, 10 pages.

Patel et al., "Selective inhibitors 1-15 of dual leucine zipper kinase (DLK, MAP3K12) with activity in a model of alzheimer's disease," Journal of Medicinal Chemistry, vol. 60, No. 19, Sep. 20, 2017, pp. 8083-8102, XP55971460.

International Search Report and Written Opinion issued by the International Searching Authority for Application No. PCT/2020/018161, dated Jul. 17, 2020, 25 pages.

Blacklowe, Neil R., "Parvovires and Human Disease," J. R. Pattison, ed, pp. 165-174 (1988).

Berns, Kenneth I., "Parvoviridae and Their Replication", Virology Chapter 62, Raven Press, 1990, pp. 1743-1764.

Carter et al., "AAV DNA Replication, Integration, and Genetics," Handbook of Parvovirus, vol. 1, pp. 169-228 (1990).

Castle et al., "Controlling AAV Tropism in the Nervo System with Natural and Engineered Capsids," Methods in Molecular Biology, 2016; 1382:133-149.

Choi et al., "AAV Hybrid Serotpes: Improved Vectors for Gene Delivery," Current Gene Therapy, Jun. 2005, 5(3):299-310.

Daiger et al., "Genes and mutations causing retinitis pigmentosa," Clin Genet, May 2013, 84:132-141.

De et al., "High Levels of Persistent Expression of $\alpha$1-Antitrypsin Mediated by the Non human Primate Serotype rh.10 Adeno-associated Virus Despite Preexisting Immunity to Common Human Adeno-associated Viruses," Molecular Therapy, Jan. 2006, vol. 13, No. 1, pp. 67-76.

Gao et al., "Clades of Adeno-Associated Viruses Are Widely Disseminated in Human Tissues," Journal of Virology, Jun. 2004, vol. 78, No. 12, pp. 6381-6388.

GenBank Accession No. AF085716, Feb. 1999, 3 pages.
GenBank Accession No. AX753246, Jun. 2003, 2 pages.
GenBank Accession No. AX753249, Jun. 2003, 2 pages.
GenBank Accession No. NC_001401, Aug. 2018, 6 pages.
GenBank Accession No. NC_001829, Aug. 2018, 3 pages.
GenBank Accession No. NC_001862, Jan. 1998, 8 pages.
GenBank Accession No. NC_002077, Aug. 2018, 3 pages.

Hanlon et al., "A Novel Retinal Ganglion Cell Promoter for Utility in AAV Vectors," Frontiers in Neuroscience, Sep. 21, 2017, vol. 11, Article 521, 12 pages.

Hickey et al., "Tropism of engineered and evolved recombinant AAV serotypes in the RDL mouse and ex vivo primate retina," Gene Therapy, Dec. 2017, 24(12):787-800.

Hu et al., "Differentially expressed miRNAs in hepatocellular carcinoma cells under hypoxic conditions are associated with transcription and phosphorylation," Oncology Letters, Jan. 2018, 15:467-474.

Kay et al., "Targeting Photoreceptors via Intravitreal Delivery Using Novel, Capsid-Mutated AAV Vectors," PLoS One, Apr. 26, 2013, vol. 8, Issue 4, e62097, 12 pages.

Lebherz et al., "Novel AAV serotypes for improved ocular gene transfer," The Journal of Gene Medicine, Apr. 2008, 10(4):375-382.

Loakes et al., "5-Nitroindole as an universal base analogue," Nucleic Acids Research, Oct. 1994, vol. 22, No. 20, pp. 4039-4043.

Marsic et al., "Vector Design Tour de Force: Integrating Combinatorial and Rational Approches to Derive Novel Adeno-associated Virus Variants," Molecular Therapy, Nov. 2014, vol. 22, No. 11, pp. 1900-1909.

Mata et al., "Characterization of Dual Leucine Zipper-bearing Kinase, a Mixed Lineage Kinase Present in Synaptic Terminals Whose Phosphorylation State Is Regulated by Membrane Depolarization via Calcineurin*," The Journal of Biological Chemistry, vol. 271, No. 28, Jul. 1996, pp. 16888-16896.

Mccarty et al., "Self-complementary recombinant adeno-associated virus (scAAV) vectors promote efficient transduction independently of DNA synthesis," Gene Therapy, Aug. 2001, 8 (16):1248-1254.

Mori et al., "Two novel adeno-associated viruses from cynomolgus monkey: pseudotyping characterization of capsid protein," Virology, Dec. 2004, 330(2):375-383.

Muzyczka, N., "Use of Adeno-Associated Virus as a General Transduction Vector for Mammalian Cells," Current Topics in Microbiology and Immunology, vol. 158:97-129 (1992).

Nichols et al., "A universal nucleoside for use at ambiguous sites in DNA primers," Nature, vol. 369, Jun. 1994, pp. 492-493.

Nihalani et al., "Identification of Structural and Functional Domains in Mixed Lineage Kinase Dual Leucine Zipper-bearing Kinase Required for Complex Formation and Stress-activated Protein Kinase Activation*," The Journal of Biological Chemistry, vol. 275, No. 10, Mar. 2000, pp. 7273-7279.

Qazi et al., "Corneal transparency: Genesis, maintenance and dysfunction," Brain Research Bulletin, Feb. 15, 2010; 81(2-3):198-210.

Rose, James A., "Parvovirus Reproduction," Comprehensive Virology 3: 1-61 (1974).

Schlabach et al., "Synthetic design of strong promoters," Proc Natl Acad Sci, Feb. 2010, vol. 107, No. 6, 2538-2543.

Sharma et al., "Transduction efficiency of AAV 2/6, 2/8 and 2/9 vectors for delivering genes in human corneal fibroblasts," Brain Research Bulletin 81, Feb. 2010, pp. 273-278.

Simpson et al., "New MiniPromoter Ple345 (NEFL) Drives Strong and Specific Expression in Retinal Ganglion Cells of Mouse and Primate Retina," Human Gene Therapy, vol. 30, No. 3, Mar. 2019, pp. 257-272.

Siu et al., "Dual Leucine Zipper Kinase Inhibitors for the Treatment of Neurodegeneration," J. Med. Chem. 61:8078-8087 (Jun. 2018).

Smith et al., "In vivo imaging of adeno-associated viral vector labelled retinal ganglion cells," Scientific Reports, Jan. 2018, 8:1490, 11 pages.

Srivastava et al., "Nucleotide Sequence and Organization of the Adeno-Associated Virus 2 Genome," Journal of Virology, Feb. 1983, vol. 45, No. 2, pp. 555-564.

Wang et al., "Single stranded adeno-associated virus achieves efficient gene transfer to anterior segment in the mouse eye," PLoS One, Aug. 2017, 12(8):e0182473, 12 pages.

Watkins et al., "DLK initiates a trnscriptional program that couples apoptotic and regenerative responses to axonal injury," Proc Natl Acad Sci, Mar. 2013, vol. 110, No. 10, pp. 4039-4044.

Watkins et al., "Nearest-neighbor thermodynamics of deoxyinosine pairs in DNA duplexes," Nucleic Acids Research, Nov. 2005, vol. 33, No. 19, pp. 6258-6267.

Xiong et al., "Protein turnover of the Wallenda/DLK kinase regulates a retrograde response to axonal injury," J. Cell Biol, Oct. 2010, vol. 191, No. 1, pp. 211-223.

Xu et al., "The MILK Family Mediates c-Jun N-Terminal Kinase Activation in Neuronal Apoptosis," Molecular and Cellular Biology, Jul. 2001, vol. 21, No. 14, pp. 4713-4724.

(56) References Cited

OTHER PUBLICATIONS

Ye et al., "MicroRNA-130a Targets MAP3K12 to Modulate Diabetic Endothelial Progenitor Cell Function," Cellular Physiology and Biochemistry, May 2015, 36(2):712-726.

* cited by examiner

FIG. 1B

```
----L1-----L2-----L3-----L4-----L5-----L6-----L7-----L8---
abcdefgabcdefgabcdefgabcdefgabcdefgabcdefgabcdefg
REEVKLHFEKIKSEGTCLHRLEEELVMRREELRHALDIREHYERKLERANNLYMELNALMLQLELKERELLRREQALERR
```

FIG. 3

```
----L1----L2----L3----L4----                                    ----L5----L6----L7----L8----
abcdefgabcdefgabcdefgabcdefg                                    abcdefgabcdefgabcdefgabcdefg
REEVELEFEKIRSEGTCLEREEEELEMERREEELRHALDIREHYERKLERANNLYMELNALMLQLELRERELEREEQALERR
```

FIG. 4A

```
DLK-DLK homodimer
---L1-------L2-------L3-------L4-------L5-------L6-------L7-------L8---
abcdefgabcdefgabcdefgabcdefgabcdefgabcdefgabcdefg
   K-H------K-E------H-L------V-R------N-L------E-K------L-R------E-R
    ╳                  ╳                          ╳
   K-H------K-E------H-L------V-R------N-L------E-K------L-R------E-R
```

DUAL LEUCINE ZIPPER KINASE INHIBITORS FOR GENE THERAPY

RELATED APPLICATIONS

This application is the National Stage of International Application No. PCT/US2020/018161, filed Feb. 13, 2020, which claims priority to U.S. Provisional Patent Appl. No. 62/806,213, filed Feb. 15, 2019, and U.S. Provisional Patent Appl. No. 62/806,210, filed Feb. 15, 2019, each of which is incorporated herein by reference in its entirety.

FIELD OF THE INVENTION

The present disclosure relates generally to cellular or gene therapy using an engineered inhibitor of Dual Leucine Zipper Kinase, including for neurodegenerative disorders such as glaucoma.

SEQUENCE LISTING

The instant application contains a Sequence Listing which has been submitted in ASCII format via EFS-Web and is hereby incorporated by reference in its entirety. Said ASCII copy, created on Mar. 7, 2022, is named "EXHA-002_01US_SeqList.txt" and is about ~41 kilobytes in size.

BACKGROUND OF THE INVENTION

Dual Leucine Zipper Kinase (DLK) a member of the serine/threonine protein kinase family encoded, in humans, by the DLK gene, also known as Mitogen-Activated Protein Kinase Kinase Kinase 12 or MAP3K12. This kinase contains a leucine-zipper domain and is predominately expressed in neuronal cells. The phosphorylation state of this kinase in synaptic terminals was shown to be regulated by membrane depolarization via calcineurin. This kinase forms homodimers, as well as heterodimers with leucine zipper containing transcription factors, such as cAMP responsive element binding protein (CREB) and MYC, and thus may play a regulatory role in PKA or retinoic acid induced neuronal differentiation. Alternatively spliced transcript variants encoding different proteins have been described. Expression of DLK with a K152A point mutation in the active site of the kinase results has a dominant negative affect on endogenous DLK. Xu et al. Mol Cell Biol. 21(14):4713-24 (2001).

DLK has been shown to be an essential component of neuronal response to axon damage. DLK protein is present in axons, and protein levels are increased in response to axonal injury (Xiong X, et al. J. Cell Biol, 2010; 191(1): 211-223). DLK initiates a transcriptional program that couples apoptotic and regenerative responses to axonal injury (Watkins et al., Proc Natl Acad Sci, 2013; 110(10): 4039-4044).

Optic neuropathies are a group of vision diseases related to neuronal cell death, specifically the death of projection neurons called retinal ganglion cells (RGCs). Among the optic neuropathies, the U.S. spends $1.9 billion per annum to treat glaucoma.

Thus, there is a long-felt yet unmet need for compositions and methods for treating diseases or disorders related to DLK and for compositions and methods for cellular or gene therapy for glaucoma. The disclosure provides such novel compositions and methods to address and solve this need.

SUMMARY OF THE INVENTION

The present disclosure provides various embodiments of inhibitors of DLK, e.g., inhibitors of DLK that act in a dominant negative fashion by forming inactive heterodimers with endogenous DLK, called Dominant-Negative Dual Leucine Zipper Kinases (DN-DLKs).

In one aspect, the disclosure provides compositions and methods useful for treating diseases or disorders related to DLK and to retinal cells. In particular, the disclosure provides vectors (including viral vectors) for delivery of DN-DLKs, methods of using such vectors in treatment, and methods of inhibiting DLK activity in cells.

In some embodiments, the disclosure provides inhibitors that comprises a sequence at least 95% identical to the leucine zipper domain of DLK (SEQ ID NO: 3) with substitutions in at least one of positions 391 and 393, using the numbering of full-length, human DLK (SEQ ID NO: 1).

The disclosure also provides recombinant virus vectors, including recombinant adeno-associated virus (rAAV) vectors, comprising an expression cassette whose polynucleotide sequence encodes one of the inhibitors of the disclosure.

The disclosure also provides methods of inhibiting DLK activity in a cell using the vectors, as well as pharmaceutical compositions and unit doses that include vector(s) of the disclosure. The disclosure further provides methods of treatment for conditions including, without limitation, diseases or disorders related to dysfunction in retinal cells is selected from the group consisting of glaucoma, wet macular degeneration, dry macular degeneration, geographic atrophy, retinal detachment, and retinal dystrophy, such as Usher's syndrome, Stargardt's disease, Leber's congenital amaurosis, or retinitis pigmentosa. In yet other embodiments, the disease is related to retinopathy, such as diabetic retinopathy, myopic maculopathy. In other embodiments, the disease is an optic neuropathy, such as optic neuritis, non-arteritic anterior ischemic optic neuropathy (NAION), arteritic anterior ischemic optic neuropathy (AION), traumatic optic neuropathy, Leber's optic neuropathy, dominant optic atrophy, recessive optic atrophy, or radiation optic neuropathy. In other embodiments, the disease may include one or more of amyotrophic lateral sclerosis (ALS), Parkinson Disease, Alzheimer Disease, prion-related neurodegenerative disease, Huntington's disease, spinocerebellar ataxia, spinal muscular atrophy, and multiple system atrophy.

In another aspect, the disclosure provides vectors that comprise a polynucleotide encoding an inhibitor of Dual Leucine Zipper Kinase (DLK). The polynucleotide may be operatively linked to a promoter. The inhibitor is capable of binding either (i) an endogenous DLK protein, or (ii) an endogenous mRNA encoding an endogenous DLK. In some embodiments, the inhibitor is capable of reducing the expression, signaling activity, or kinase activity of the endogenous DLK in a retinal cell. The disclosure also provides methods of treating diseases or disorders related to retinal cells that involve administering such vectors to the retina of a subject. Diseases or disorders that can be treated include, with limitation, diseases or disorders related to dysfunction in retinal cells. Examples include glaucoma, retinopathy, retinal detachment, optic neuropathies, and retinal dystrophy.

The disclosure also provides a genetically modified retinal cell that includes the types of polynucleotides already described, ones encoding an inhibitor of Dual Leucine Zipper Kinase (DLK). The disclosure provides methods of making such cells, including contacting them with a viral vector. Pharmaceutical compositions are also provided herein.

The foregoing paragraphs are not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. The invention includes, as an additional aspect, all embodiments of the invention narrower in scope in any way than the variations defined by specific paragraphs above. For example, where certain aspects of the invention that are described as a genus, it should be understood that every member of a genus is, individually, an aspect of the invention.

BRIEF DESCRIPTION OF THE DRAWINGS

FIGS. 1A-1B depict the leucine zipper domain of dual leucine zipper kinase (DLK). FIG. 1A shows a schematic depiction of the dimerization of a single heptad repeat of a leucine zipper. Amino acid residues within the heptad on one monomer are represented by letters (a) through (g) in N-terminal to C-terminal direction. The equivalent positions on the other monomer are represented by letters (a') through (g'). The pairs formed between e on one strand of the dimer, and g' on the opposite strand (called e-g' or e'-g pairs) can form electrostatic interactions and are important in determining the stability of the leucine zipper dimer. FIG. 1B shows the amino-acid sequence of residues 387 to 467 of human DLK (SEQ ID NO: 4) (also known as MAP3K12), according to isoform 1 numbering (UniProt Q12852). The eight heptad repeats are labeled L1 through L8, and each residues with in the repeat is labeled a through g, following the convention shown in FIG. 1A.

FIG. 3 depicts a designed dominant-negative DLK (DN-DLK) construct (SEQ ID NO: 6). Substitutions with respect to native DLK are shown underlined and bold.

FIG. 4A-4C depicts the homo- or hetero-dimerization interactions of DLK and the DN-DLN of FIG. 3. Only g and e residues are shown to highlight g-e' and g'-e interactions. Electrostatic interactions are depicts by lines. Interactions between opposite charges are shown as bolded solid lines to indicate attractive force. Interactions between like charges are shown as dashed lines to indicate repulsive force. FIG. 4A shows a homodimer of DLK. FIG. 4B shows a heterodimer of DLK and DN-DLK. FIG. 4C shows a homodimer of DN-DLK.

DETAILED DESCRIPTION

1. Overview

Figure 1A:
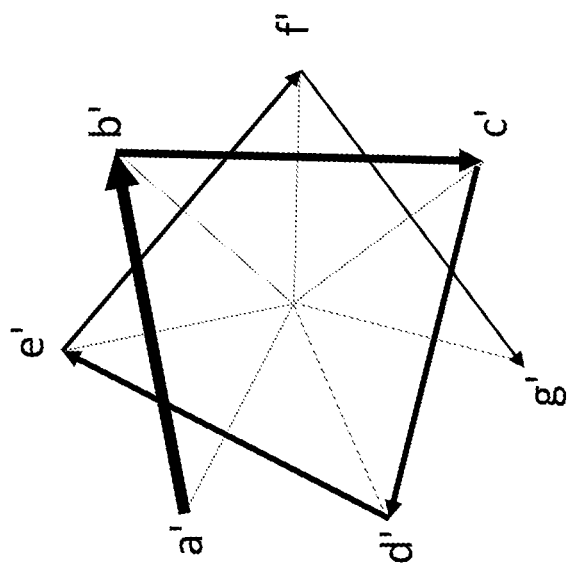
Figure 1A:
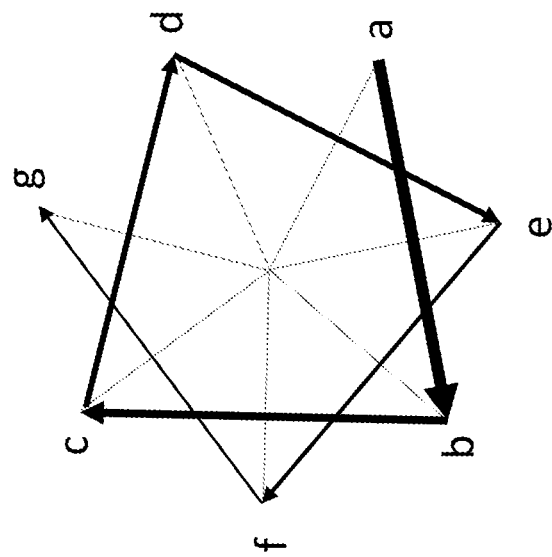
Figure 2A:
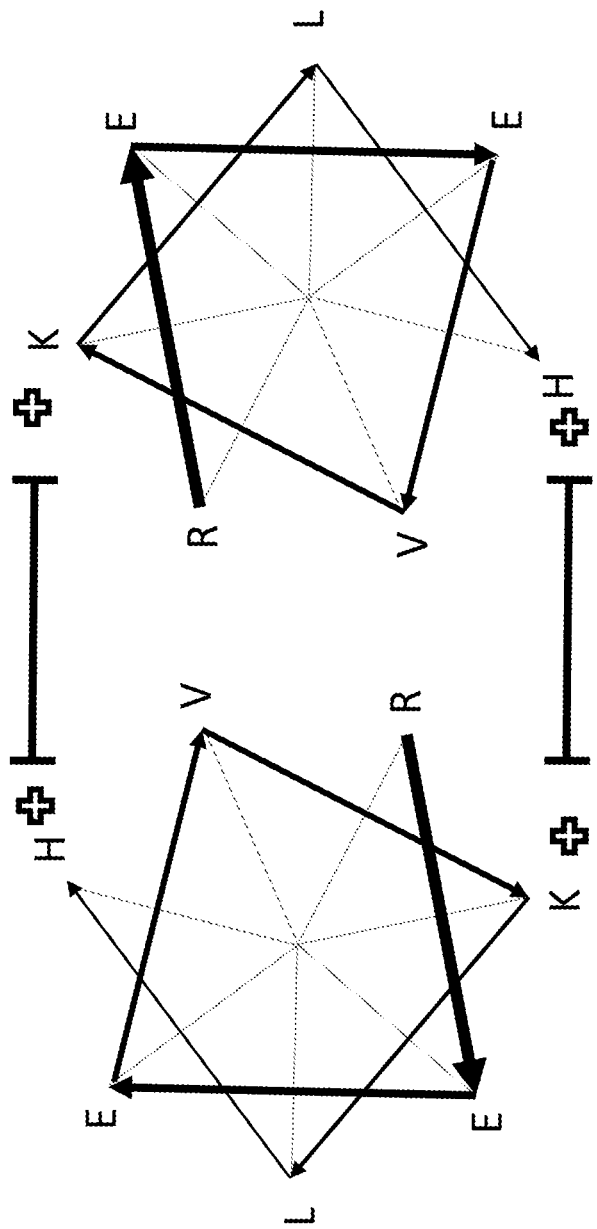
FIGS. 2A-2H depict the eight heptad repeats L1 (FIG. 2A), L2 (FIG. 2B), L3 (FIG. 2C), L4 (FIG. 2D), L5 (FIG. 2E), L6 (FIG. 2F), L7 (FIG. 2G), L8 (FIG. 2H). In the native homodimer of DLK each of the heptad repeats homodimerizes with the equivalent heptad (L1 with L1, L2 with L2, etc.). In each panel, the dimerization of one heptad is shown in the standard helical wheel representation as shown in FIG. 1A. Standard one-letter abbreviation are used in for each amino acid position. The character of the amino acid at key positions are indicated as positive (+), negative (−), or hydrophobic (hydro). The g-e' and e-g' interactions are indicated by blocking arrows (repulsive or charged-hydrophobic interactions) or pointing arrows (charge-charge attractive forces) at the center top or center bottom of each panel.
Figure 2B:
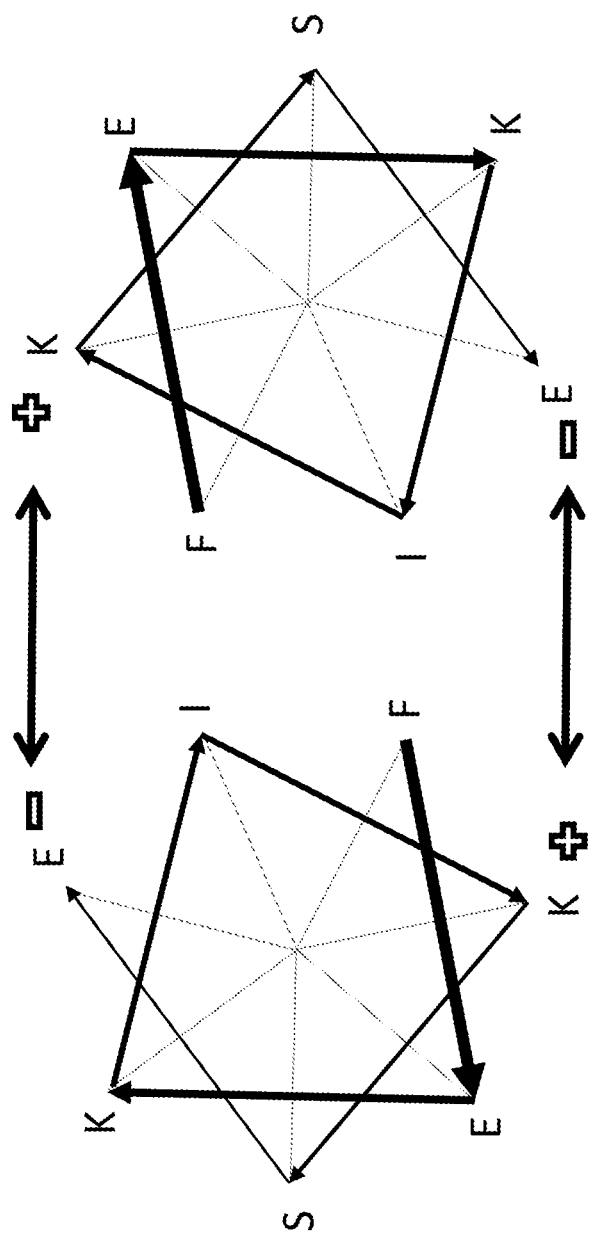
Figure 2C:
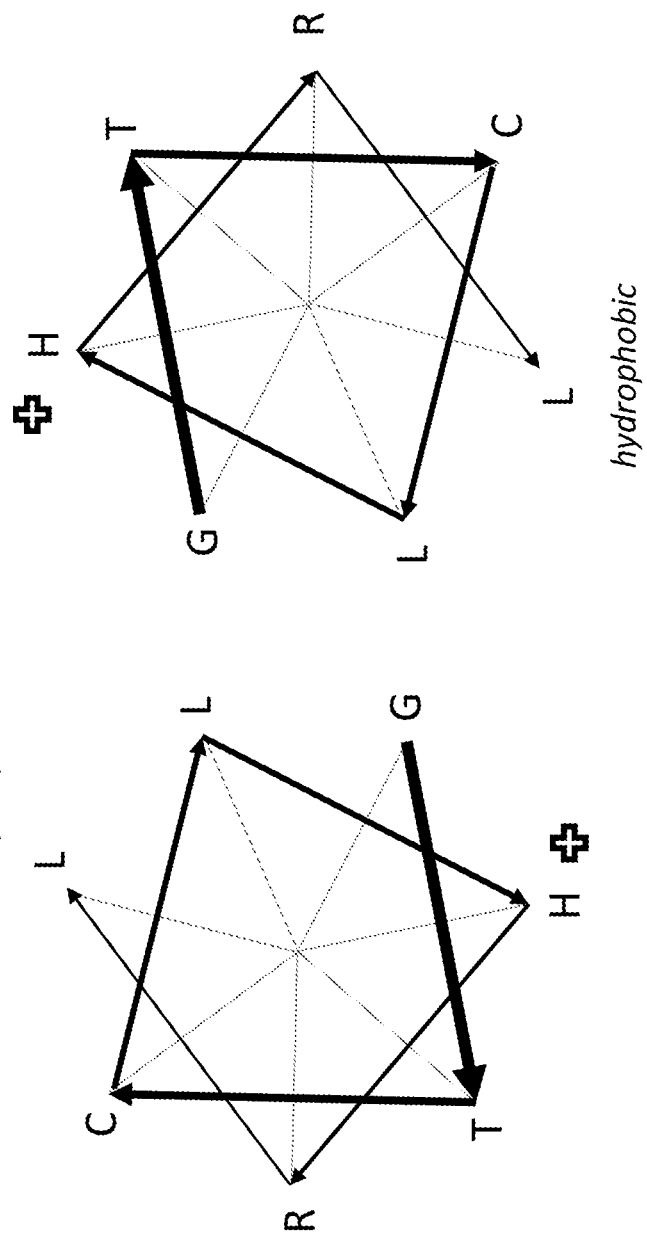
Figure 2D:
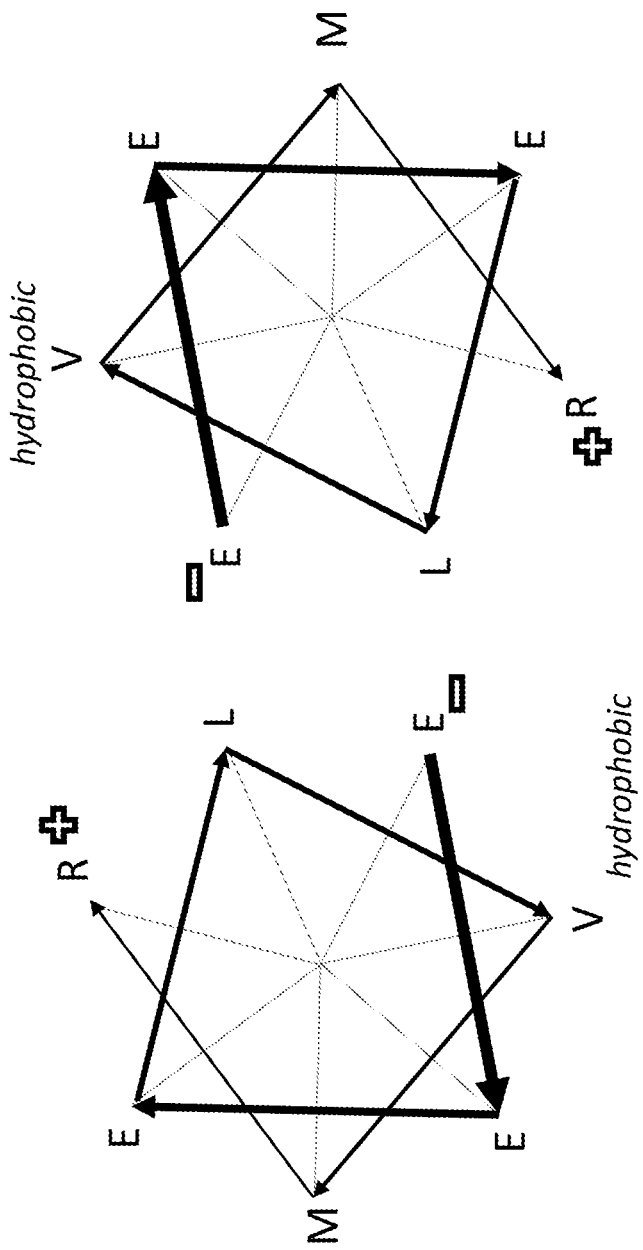
Figure 2E:
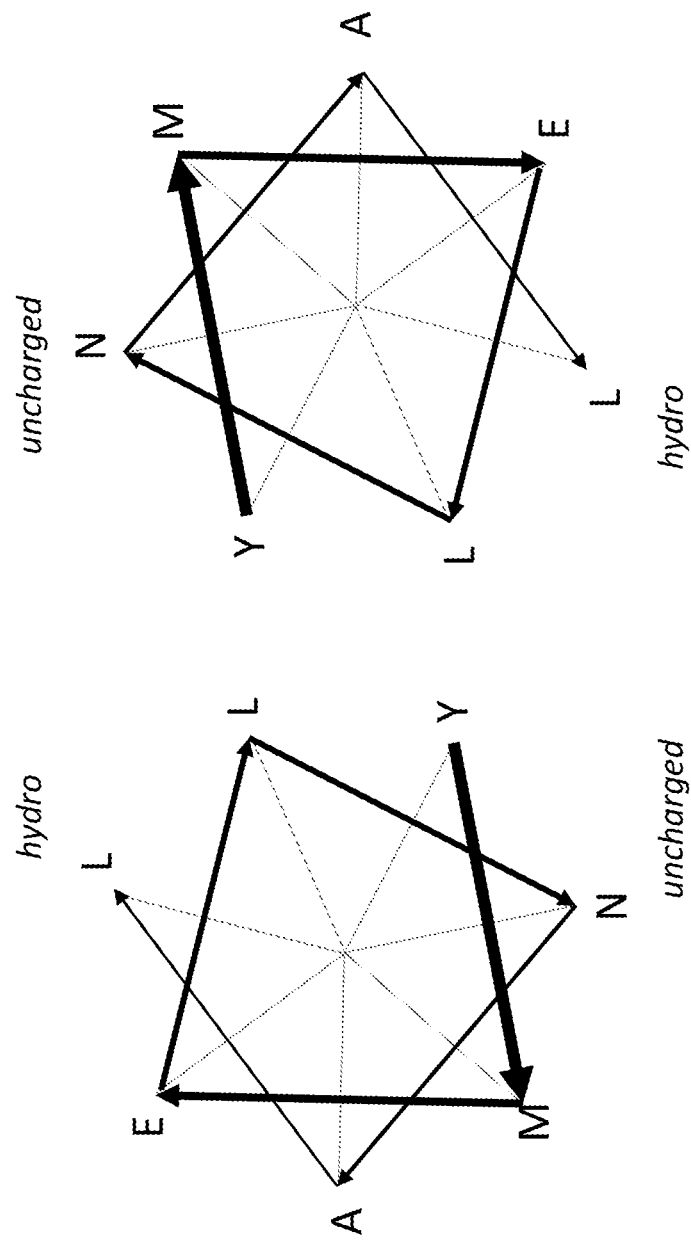
Figure 2F:
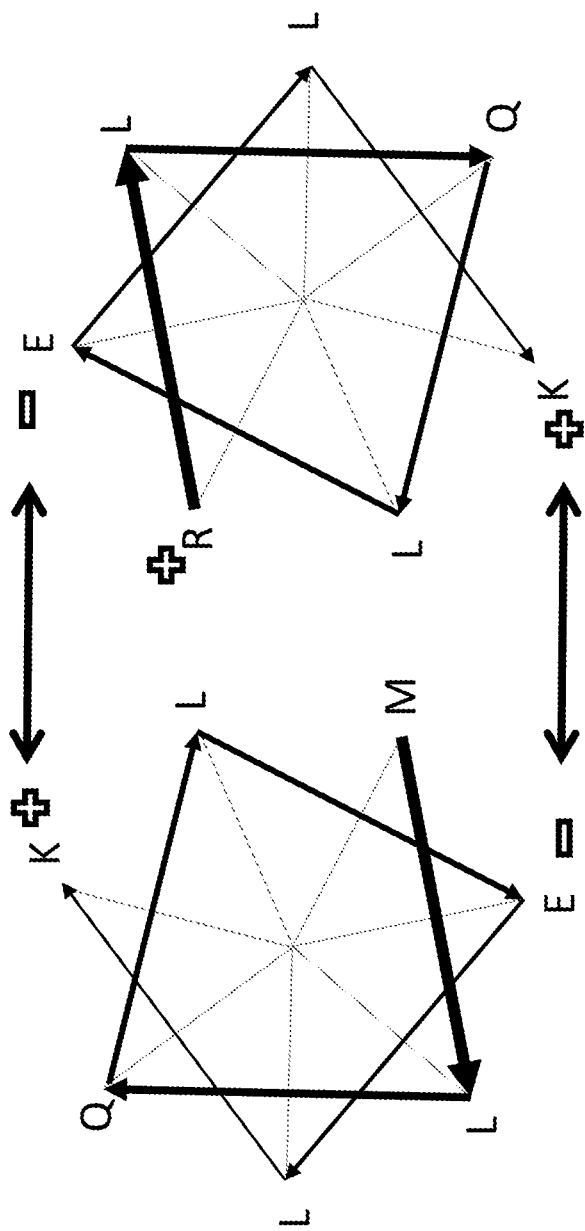
Figure 2G:
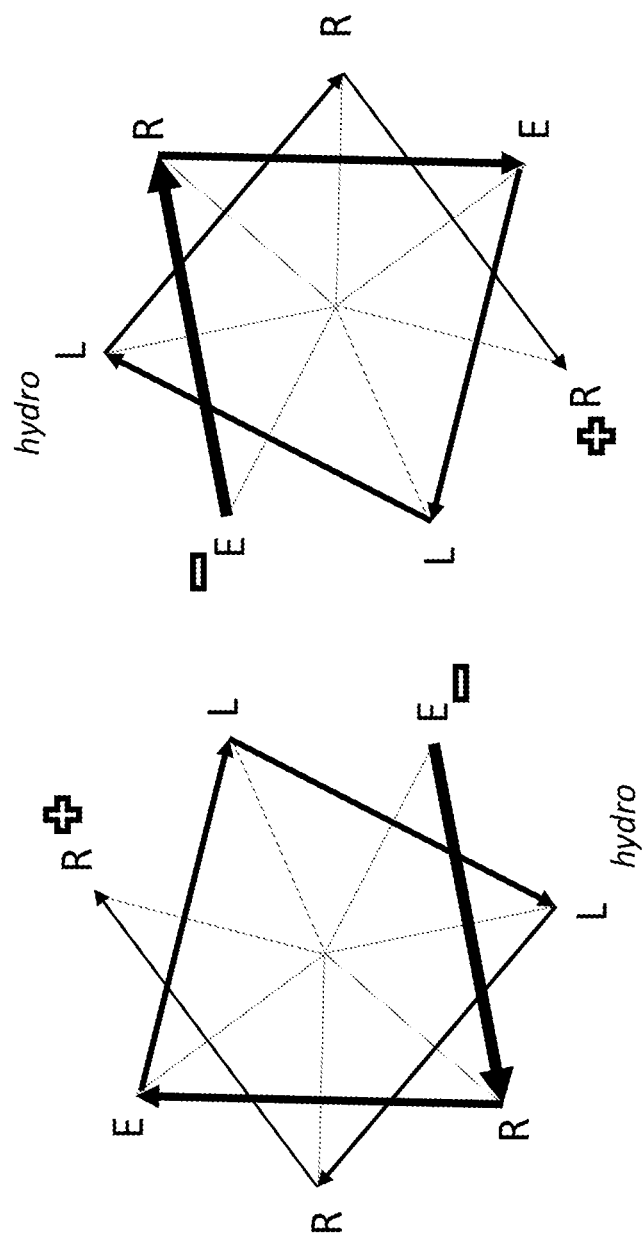
Figure 2H:
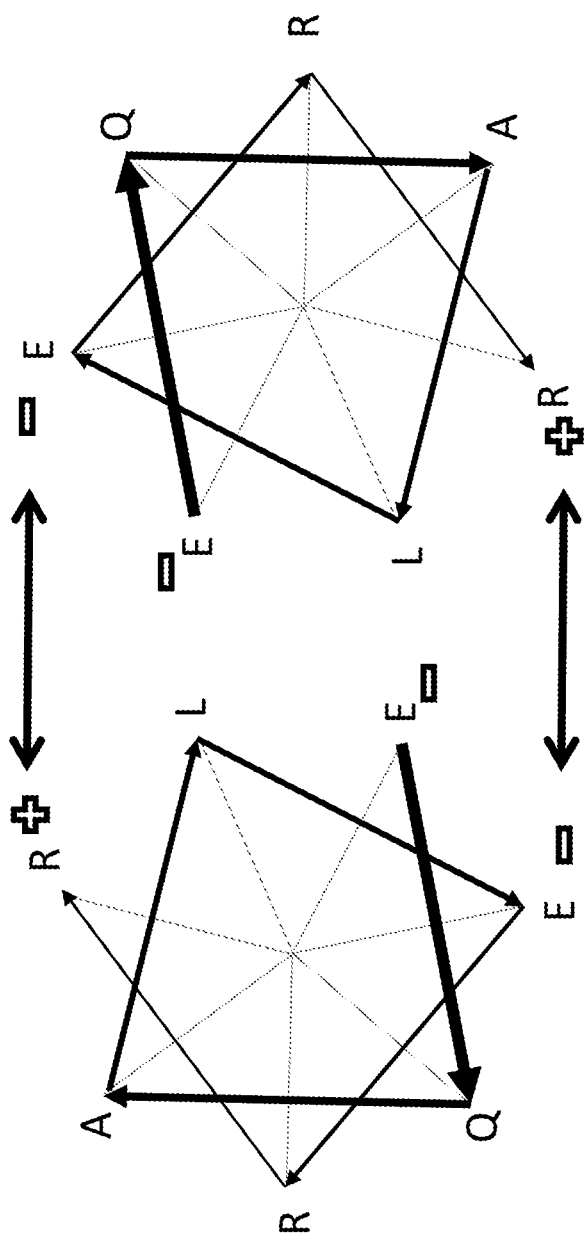
Figure 4B:
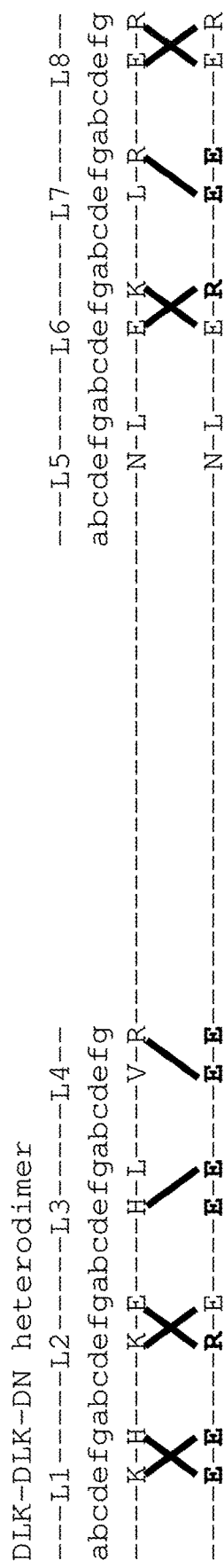
Figure 4C:

The disclosure provides compositions and methods useful for treating diseases or disorders related to retinal cells. In particular, the invention provides cells and vectors comprising a polynucleotide encoding an inhibitor of Dual Leucine Zipper Kinase (DLK), and method of use thereof. Advantageously, the vector is capable of reducing the expression, signaling activity, or kinase activity of the endogenous DLK in a cell, which is, in some embodiments, a retinal cell.

2. Definitions

All publications and patents mentioned herein are hereby incorporated by reference in their entirety as if each individual publication or patent was specifically and individually indicated to be incorporated by reference. In case of conflict, the present application, including any definitions herein, will control. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. The term "about", when immediately preceding a number or numeral, means that the number or numeral ranges plus or minus 10%. It should be understood that the terms "a" and "an" as used herein refer to "one or more" of the enumerated components unless otherwise indicated. The use of the alternative (e.g., "or") should be understood to mean either one, both, or any combination thereof of the alternatives. The term "and/or" should be understood to mean either one, or both of the alternatives. As used herein, the terms "include" and "comprise" are used synonymously.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Decrease" or "reduce" refers to a decrease or a reduction in a particular value of at least 5%, for example, 5, 6, 7, 8, 9, 10, 15, 20, 25, 30, 35, 40, 45, 50, 55, 60, 65, 70, 75, 80, 85, 90, 95, 99 or 100% as compared to a reference value. A decrease or reduction in a particular value may also be represented as a fold-change in the value compared to a reference value, for example, at least 1, 2, 3, 4, 5, 6, 7, 8, 9, 10, 15, 20, 30, 40, 50, 60, 70, 80, 90, 100, 200, 500, 1000-fold, or more, decrease as compared to a reference value.

"Increase" refers to an increase in a particular value of at least 5%, for example, 5, 6, 7, 8, 9, 10, 15, 20, 25, 30, 35, 40, 45, 50, 55, 60, 65, 70, 75, 80, 85, 90, 95, 99, 100, 200, 300, 400, 500% or more as compared to a reference value. An increase in a particular value may also be represented as a fold-change in the value compared to a reference value, for example, at least 1-fold, 2, 3, 4, 5, 6, 7, 8, 9, 10, 15, 20, 30, 40, 50, 60, 70, 80, 90, 100, 200, 500, 1000-fold or more, increase as compared to the level of a reference value.

"Complementary" refers to the capacity for pairing, through base stacking and specific hydrogen bonding, between two sequences comprising naturally or non-naturally occurring (e.g., modified as described above) bases (nucleosides) or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and SantaLucia, Nucl. Acids Research, 2005; 33 (19): 6258-6267.

The term "subject" includes animals, such as e.g. mammals. In some embodiments, the mammal is a primate. In some embodiments, the mammal is a human. In some embodiments, subjects are livestock such as cattle, sheep, goats, cows, swine, and the like; or domesticated animals such as dogs and cats. In some embodiments (e.g., particularly in research contexts) subjects are rodents (e.g., mice, rats, hamsters), rabbits, primates, or swine such as inbred pigs and the like. The terms "subject" and "patient" are used interchangeably herein.

"Administration" refers herein to introducing an agent or composition into a subject.

"Treating" as used herein refers to delivering an agent or composition to a subject to affect a physiologic outcome. In some embodiments, treating refers to the treatment of a disease in a subject, e.g., in a human, including (a) inhibiting the disease, e.g., arresting disease development or preventing disease progression; (b) relieving the disease, e.g., causing regression of the disease state; (c) curing the disease; and (d) preventing onset of disease, e.g., arresting disease development in an asymptomatic subject identified as a carrier of a genetic defect. In one aspect, treatment excludes prophylaxis or prevention.

The term "effective amount" or "therapeutically effective amount" refer to the minimum amount of an agent or composition required to result in a particular physiological effect (e.g., an amount required to increase, activate, or enhance a particular physiological effect). The effective amount or therapeutically effective amount of a particular agent may be represented in a variety of ways based on the nature of the agent, such as mass/volume, # of cells/volume, particles/volume, (mass of the agent)/(mass of the subject), # of cells/(mass of subject), or particles/(mass of subject). The effective amount or therapeutically effective amount of a particular agent may also be expressed as the half-maximal effective concentration ($EC_{50}$), which refers to the concentration of an agent that results in a magnitude of a particular physiological response that is half-way between a reference level and a maximum response level.

"Population" of cells refers to any number of cells greater than 1, but is preferably at least $1\times10^3$ cells, at least $1\times10^4$ cells, at least at least $1\times10^5$ cells, at least $1\times10^6$ cells, at least $1\times10^7$ cells, at least $1\times10^8$ cells, at least $1\times10^9$ cells, at least $1\times10^{10}$ cells, or more cells. A population of cells may refer to an in vitro population (e.g., a population of cells in culture) or an in vivo population (e.g., a population of cells residing in a particular tissue).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans and/or domestic animals.

As used herein "vector" refers to a nucleic acid molecule capable transferring or transporting a nucleic acid molecule to cell, along with, in a viral vector, one or more viral proteins, such as for encapsulated viruses the capsid of the virus. The transferred nucleic acid is generally linked to, e.g., inserted into, the vector nucleic acid molecule. A vector may include sequences that direct autonomous replication or reverse transcription in a cell, or may include sequences sufficient to allow integration into host cell DNA. "Vectors" include gene therapy vectors. As used herein, the term "gene therapy vector" refers to a vector capable of use in performing gene therapy, e.g., delivering a polynucleotide sequence encoding a therapeutic polypeptide to a subject. Gene therapy vectors may comprise a polynucleotide ("transgene") encoding a protein.

As used herein, the term "expression cassette" refers to a DNA segment that is capable in an appropriate setting of driving the expression of a polynucleotide (e.g., a transgene) encoding a protein that is incorporated in said expression cassette. When introduced into a host cell, an expression cassette inter alia is capable of directing the cell's machinery to transcribe the transgene into RNA, which is then usually further processed and finally translated into the therapeutically active polypeptide. The gene therapy vector can comprise, or consist essentially of expression cassette. The term expression cassette excludes polynucleotide sequences 5' to the 5' ITR and 3' to the 3' ITR. Provided herein are host cells comprising, or consisting essentially of, or yet further consisting of the vector of this disclosure. The cells can be of any appropriate species, e.g., mammalian cells.

As used herein, the phrases "operably linked" or "under the transcriptional control" with respect to a polynucleotide refers, interchangeably, to a configuration of the promoter and the polynucleotide that enables the polynucleotide to be transcribed by a polymerase capable of binding to the promoter.

The term "sequence identity" refers to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared. A polynucleotide or polynucleotide region (or a polypeptide or polypeptide region) having a certain percentage (for example, 60%, 65%, 70%, 75%, 80%, 85%, 90%, 95%, 98% or 99%) of "sequence identity" to a reference sequence means that, when aligned, that percentage of bases (or amino acids) at each position in the test sequence are identical to the base (or amino acid) at the same position in the reference sequence. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/blast/Blast.cgi.

An "equivalent" or "functional equivalent" of a polypeptide or protein is one that has a certain sequence identity to that reference polypeptide or protein, (for example, 60%, 65%, 70%, 75%, 80%, 85%, 90%, 95%, 98% or 99% identity to the reference) and retains similar activity or function compared to the reference polypeptide or protein.

"Comprising" or "comprises" is intended to mean that the compositions, for example media, and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this disclosure.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

The section headings used herein are for organizational purposes only and are not to be construed as limiting the subject matter described.

3.1 Vectors

Various embodiments of the invention include viral vectors and non-viral vectors. Viral vectors include adeno-associated virus, adenovirus, lentivirus, Sleeping Beauty, herpesvirus, and other viruses known in the art. It is within the skill of the ordinary artisan to adapt the polynucleotides of the invention to various viral vectors. Non-viral vectors include liposomes, lipid-like particles, and cationic polymers, as well as electroporation of naked DNA in plasmid, bacmid, linear, mincircular or other form. The polynucleotides of the disclosure may be delivered as either DNA or RNA. Modified polynucleotides are known in the art and are included methods and compositions of the present disclosure. The disclosure of particular types of viral and non-viral vectors in particular embodiments described herein is not intended as limiting the invention.

As used herein, the term "AAV" is a standard abbreviation for adeno-associated virus or a recombinant vector thereof. Adeno-associated virus is a single-stranded DNA parvovirus that grows only in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). It is fully expected that the same principles described in these reviews will be applicable to additional AAV serotypes characterized after the publication dates of the reviews because it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

As used herein, an "AAV vector" or "rAAV vector" refers to a recombinant vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

As used herein, an "AAV virion" or "AAV viral particle" or "AAV vector particle" refers to a viral particle composed of at least one AAV capsid protein and an encapsidated polynucleotide AAV vector. As used herein, if the particle comprises a heterologous polynucleotide (i.e. a polynucleotide other than a wild-type AAV genome such as a transgene to be delivered to a mammalian cell), it is typically referred to as an "AAV vector particle" or simply an "AAV vector." Thus, production of AAV vector particle necessarily includes production of AAV vector, as such a vector is contained within an AAV vector particle.

Adeno-associated virus (AAV) is a replication-deficient parvovirus, the single-stranded DNA genome of which is about 4.7 kb in length including two 145 nucleotide inverted terminal repeat (ITRs). There are multiple known variants of AAV, also sometimes called serotypes when classified by antigenic epitopes. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45:555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78:6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in U.S. Pat. No. 9,434,928, incorporated herein by reference. The sequence of ancestral AAVs including AAV.Anc80, AAV.Anc80L65 and their derivatives are described in WO2015054653A2 and Wang et al. Single stranded adeno-associated virus achieves efficient gene transfer to anterior segment in the mouse eye. PLoS One. 2017 Aug. 1; 12(8):e0182473.

AAV vectors may refer to either naturally occurring AAVs, such as AAV-1 to AAV-10, or non-naturally occurring vectors, such as those that have been engineered through rational design, directed evolution, and the like. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p9), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158:97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

3.2 AAV Serotypes and Genomes

AAV DNA in the rAAV genomes may be from any AAV variant or serotype for which a recombinant virus can be derived including, but not limited to, AAV variants or serotypes AAV-1, AAV-2, AAV-3, AAV-4, AAV-5, AAV-6, AAV-7, AAV-8, AAV-9, AAV-10, AAV-11, AAV-12, AAV-13 and Anc80L65. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). The nucleotide sequences of the genomes of various AAV serotypes are known in the art. To promote eye-specific expression, AAV6, AAV8 or AAV9 may be used.

In some cases, the rAAV comprises a self-complementary genome. As defined herein, an rAAV comprising a "self-complementary" or "double stranded" genome refers to an rAAV which has been engineered such that the coding region of the rAAV is configure to form an intra-molecular double-stranded DNA template, as described in McCarty et al. Self-complementary recombinant adeno-associated virus (scAAV) vectors promote efficient transduction independently of DNA synthesis. *Gene Therapy.* 8 (16): 1248-54 (2001). The present disclosure contemplates the use, in some cases, of an rAAV comprising a self-complementary genome because upon infection (such transduction), rather than waiting for cell mediated synthesis of the second strand of the rAAV genome, the two complementary halves of scAAV will associate to form one double stranded DNA (dsDNA) unit that is ready for immediate replication and transcription. It will be understood that instead of the full coding capacity found in rAAV (4.7-6 kb), rAAV comprising a self-complementary genome can only hold about half of that amount (≈2.4 kb).

In other cases, the rAAV vector comprises a single stranded genome. As defined herein, a "single standard" genome refers to a genome that is not self-complementary. In most cases, non-recombinant AAVs are have singled stranded DNA genomes. There has been some indications that rAAVs should be scAAVs to achieve efficient transduction of cells, such as ocular cells. The present disclosure contemplates, however, rAAV vectors that maybe have singled stranded genomes, rather than self-complementary genomes, with the understanding that other genetic modifications of the rAAV vector may be beneficial to obtain optimal gene transcription in target cells. In some cases, the present disclosure relates to single-stranded rAAV vectors capable of achieving efficient gene transfer to anterior segment in the mouse eye. See Wang et al. Single stranded adeno-associated virus achieves efficient gene transfer to anterior segment in the mouse eye. PLoS ONE 12(8): e0182473 (2017).

In some cases, the rAAV vector is of the serotype AAV1, AAV2, AAV4, AAV5, AAV6, AAV7, AAV8, AAV9, AAV10, AAV11, AAV12, AAV13, AAV2.7m8, or Anc80L65. Anc80L65 is described in Sharma et al. Transduction efficiency of AAV 2/6, 2/8 and 2/9 vectors for delivering genes in human corneal fibroblasts. PLoS ONE 12(8): e0182473 (2017). Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014). In some cases, the rAAV vector is of the serotype AAV9. In some embodiments, said rAAV vector is of serotype AAV9 and comprises a single stranded genome. In some embodiments, said rAAV vector is of serotype AAV9 and comprises a self-complementary genome. In some embodiments, a rAAV vector comprises the inverted terminal repeat (ITR) sequences of AAV2. In some embodiments, the rAAV vector comprises an AAV2 genome, such that the rAAV vector is an AAV-2/9 vector, an AAV-2/6 vector, or an AAV-2/8 vector. Other combinations of genome and serotype are contemplated by the present disclosure, including, without limitation, non-naturally occurring variants made by rational design, directed evolution, and the like, and those described in. *Brain Res Bull.* 2010 Feb. 15; 81 (2-3): 273; Castle et al. Controlling AAV Tropism in the Nervous System with Natural and Engineered Capsids. *Methods Mol Biol.* 2016; 1382:133-149; and Kay et al. Targeting Photoreceptors via Intravitreal Delivery Using Novel, Capsid-Mutated AAV Vectors. *PLoS One.* 2013 Apr. 26; 8(4):e62097.

3.3 Promoters

In some cases, a polynucleotide sequence encoding a transgene is operatively linked to an inducible promoter. A polynucleotide sequence operatively linked to an inducible promoters may be configured to cause the polynucleotide sequence to be transcriptionally expressed or not transcriptionally expressed in response to addition or accumulation of an agent or in response to removal, degradation, or dilution of an agent. The agent may be a drug. The agent may be tetracycline or one of its derivatives, including, without limitation, doxycycline. In some cases, the inducible promoter is a tet-on promoter, a tet-off promoter, a chemically-regulated promoter, a physically-regulated promoter (i.e. a promoter that responds to presence or absence of light or to low or high temperature). This list of inducible promoters is non-limiting.

In some embodiments, the polynucleotide sequence encoding the transgene is operably linked to a CMV promoter. The present disclosure further contemplates the use of other promoter sequences. Promoters useful in embodiments of the present disclosure include, without limitation, cytomegalovirus (CMV) and murine stem cell virus (MSCV), phosphoglycerate kinase (PGK), a promoter sequence comprised of the CMV enhancer and portions of the chicken beta-actin promoter and the rabbit beta-globin gene (CAG), a CBh promoter, a promoter sequence comprised of portions of the SV40 promoter and CD43 promoter (SV40/CD43), and a synthetic promoter that contains the U3 region of a modified MoMuLV LTR with myeloproliferative sarcoma virus enhancer (MND). In some cases, the promoter may be a synthetic promoter. Exemplary synthetic promoters are provided by Schlabach et al. Synthetic design of strong promoters. Proc Natl Acad Sci USA. 2010 Feb. 9; 107(6): 2538-2543.

In some embodiments, the polynucleotide sequence encoding the transgene is operably linked to a Nefh promoter, as described in Hanlon et al. *Front Neurosci.* 11:521 (2017) (PMID: 28983234). In some embodiments, the polynucleotide sequence encoding the transgene is operably linked to a DCX promoter, as described in Smith et al. Sci. Rep. 8:1490 (2018) (PMID: 29367685). In some embodiments, the polynucleotide sequence encoding the transgene is operably linked to a Thy1 promoter, a rhodopsin promoter, a rhodopsin kinase promoter, a pR2.1 promoter, or a MNTC promoter. Promoters provided by this disclosure include those described in US20180100165A1, US20180066022A1, US20180258446A1, US20150259395A1, US20140248701A1, US20120278912A1, WO2006108201A1, the disclosures of each of which are incorporated by reference herein in their entireties.

3.4 Dual-Leucine Zipper Kinase (DLK)

As used herein, the terms "dual-leucine zipper kinase" or "DLK" refers to the kinase, also known in the art as Mitogen-activated protein kinase kinase kinase 12 (MAP3K12), encoded by the DLK gene. DLK is a member of the Mixed Lineage Kinase (MLK). MLKs were identified initially as signaling molecules in the nervous system. They were also shown to play a role in the cell cycle. Like other MLKs, DLK has a kinase catalytic domain followed C-terminally by two leucine/isoleucine zippers separated by a short space sequence. Mata et al. *J. Bio. Chem.* 271, 16888-16896 (1996).

DLK is predominately expressed in neuronal cells. The phosphorylation state of this kinase in synaptic terminals was shown to be regulated by membrane depolarization via calcineurin. This kinase forms heterodimers with leucine zipper containing transcription factors, such as cAMP responsive element binding protein (CREB) and MYC, and thus may play a regulatory role in PKA or retinoic acid induced neuronal differentiation.

Table 1 provides the native protein sequence of human DLK, isoform 1 and isoform 2. DLKs from other species may be used in the present invention. Through the disclosure, the numbering of human isoform 1 is used. Table 1 also provides other protein sequences. Table 2 provides corresponding polynucleotide sequences, including expression cassettes and vectors. The polynucleotides disclosed can be used in various viral and non-viral vectors. In particular, the AAV genome provided as SEQ ID NO: 22 may be provided either as a plasmid for use in generating a viral particle or as a constituent of a pre-formed viral particle. It is well within the skill of those in the art to modify these sequences, such as by codon optimization, removal of spurious start or stop codons, reducing G/C content, removal of CpG dinucleotides or CpG islands, substitutions of promoter or other genetic elements, use of lentiviral LTRs rather than AAV ITRs, etc. Such polynucleotides are themselves embodiments of this disclosure.

The AAV genome disclosed as SEQ ID NO: 22 has a total length of 4099 bp. In some embodiments, SEQ ID NO: 22 is modified by insert of other polynucleotides between the flanking ITRs to increase the length of the sequence to about 4.2 to about 4.5 kilobases, in line with the expectation that this size is optimal in some contexts for AAV vectors, provided modification of SEQ ID NO: 22 does not disrupt the function of the polynucleotide sequence as an AAV genome. The disclosure contemplates substitution of various coding regions for DLK inhibitors into SEQ ID NO: 22, or into other viral genomes, including into other AAV genomes.

TABLE 1

Exemplary Dual-Leucine Zipper Kinase Sequences

| Sequence description | Sequence | SEQ ID NO |
|---|---|---|
| DLK/Map3k12 (variant 2, aka isoform 1) | MACLHETRTPSPSFGGFVSTLSEASMRKLDPDTSDCTPE KDLTPTHVLQLHEQDAGGPGGAAGSPESRASRVRADEV RLQCQSGSGFLEGLFGCLRPVWTMIGKAYSTEHKQQQE DLWEVPFEEILDLQWVGSGAQGAVFLGRFHGEEVAVKK VRDLKETDIKHLRKLKHPNIITFKGVCTQAPCYCILMEFC AQGQLYEVLRAGRPVTPSLLVDWSMGIAGGMNYLHLH KIIHRDLKSPNMLITYDDVVKISDFGTSKELSDKSTKMSF AGTVAWMAPEVIRNEPVSEKVDIWSFGVVLWELLTGEIP YKDVDSSAIIWGVGSNSLHLPVPSSCPDGFKILLRQCWN SKPRNRPSFRQILLHLDIASADVLSTPQETYFKSQAEWRE EVKLHFEKIKSEGTCLHRLEEELVMRRREELRHALDIRE HYERKLERANNLYMELNALMLQLELKERELLRREQALE RRCPGLLKPHPSRGLLHGNTMEKLIKKRNVPQKLSPHSK RPDILKTESLLPKLDAALSGVGLPGCPKGPPSPGRSRRGK TRHRKASAKGSCGDLPGLRTAVPPHEPGGPGSPGGLGG GPSAWEACPPALRGLHHDLLLRKMSSSSPDLLSAALGSR GRGATGGAGDPGSPPPARGDTPPSEGSAPGSTSPDSPGG AKGEPPPPVGPGEGVGLLGTGREGTSGRGGSRAGSQHLT PAALLYRAAVTRSQKRGISSEEEEGEVDSEVELTSSQRW PQSLNMRQSLSTFSSENPSDGEEGTASEPSPSGTPEVGST NTDERPDERSDDMCSQGSEIPLDPPPSEVIPGPEPSSLPIPH QELLRERGPPNSEDSDCDSTELDNSNSVDALRPPASLPP* | 1 |
| DLK/Map3k12 (isoform 2) | MACLHETRTPSPSFGGFVSTLSEASMRKLDPDTSDCTPE KDLTPTQCVLRDVVPLGGQGGGGPSPSPGGEPPPEPFAN SVLQLHEQDAGGPGGAAGSPESRASRVRADEVRLQCQS GSGFLEGLFGCLRPVWTMIGKAYSTEHKQQQEDLWEVP FEEILDLQWVGSGAQGAVFLGRFHGEEVAVKKVRDLKE TDIKHLRKLKHPNIITFKGVCTQAPCYCILMEFCAQGQLY EVLRAGRPVTPSLLVDWSMGIAGGMNYLHLHKIIHRDL KSPNMLITYDDVVKISDFGTSKELSDKSTKMSFAGTVAW MAPEVIRNEPVSEKVDIWSFGVVLWELLTGEIPYKDVDS SAIIWGVGSNSLHLPVPSSCPDGFKILLRQCWNSKPRNRP SFRQILLHLDIASADVLSTPQETYFKSQAEWREEVKLHFE KIKSEGTCLHRLEEELVMRRREELRHALDIREHYERKLE RANNLYMELNALMLQLELKERELLRREQALERRCPGLL KPHPSRGLLHGNTMEKLIKKRNVPQKLSPHSKRPDILKT ESLLPKLDAALSGVGLPGCPKGPPSPGRSRRGKTRHRKA SAKGSCGDLPGLRTAVPPHEPGGPGSPGGLGGGPSAWE ACPPALRGLHHDLLLRKMSSSSPDLLSAALGSRGRGATG GAGDPGSPPPARGDTPPSEGSAPGSTSPDSPGGAKGEPPP PVGPGEGVGLLGTGREGTSGRGGSRAGSQHLTPAALLY RAAVTRSQKRGISSEEEEGEVDSEVELTSSQRWPQSLNM RQSLSTFSSENPSDGEEGTASEPSPSGTPEVGSTNTDERPD ERSDDMCSQGSEIPLDPPPSEVIPGPEPSSLPIPHQELLRER GPPNSEDSDCDSTELDNSNSVDALRPPASLPP | 2 |
| DLK leucine zipper domain fragment (Nihalani et al. *J. Bio Chem.* 275, 7273-7279 (2000)) | LSTPQETYFKSQAEWREEVKLHFEKIKSEGTCLHRLEEEL VMR*RREELRHALDIREHYERKLERANNLYMELNALMLQL* ELKERELLRREQALERRCPGLLKPHPSRGLLHGNTME | 3 |
| Zipper 1, bridge, and zipper 2 from DLK | REEVKLHFEKIKSEGTCLHRLEEELVMR*RREELRHALDIR EHYERKLERANNLY*MELNALMLQLELKERELLRREQALE RR | 4 |
| Kinase domain from DLK | ILDLQWVGSGAQGAVFLGRFHGEEVAVKKVRDLKETDI KHLRKLKHPNIITFKGVCTQAPCYCILMEFCAQGQLYEV LRAGRPVTPSLLVDWSMGIAGGMNYLHLHKIIHRDLKSP NMLITYDDVVKISDFGTSKELSDKSTKMSFAGTVAWMA PEVIRNEPVSEKVDIWSFGVVLWELLTGEIPYKDVDSSAII WGVGSNSLHLPVPSSCPDGFKILLRQCWNSKPRNRPSFR QILLHLDI | 5 |

TABLE 1-continued

Exemplary Dual-Leucine Zipper Kinase Sequences

| Sequence description | Sequence | SEQ ID NO |
|---|---|---|
| Modified DLK Zipper 1, bridge, and zipper 2. Modifications in bold enhance heterodimerization with DLK, compared to DLK homodimers or LZ-LZ homodimers | REEVELEFEKIRSEGTCLEREEEELEMERREELRHALDIRE HYERKLERANNLYMELNALMLQLELRERELEREEQALER R | 6 |
| Longer LZ domain with same modifications | LSTPQETYFKSQAEWREEVELEFEKIRSEGTCLEREEEEL EMERREELRHALDIREHYERKLERANNLYMELNALMLQL ELRERELERE**EQALERRCPGLLKPHPSRGLLHGNTME | 7 |
| Kinase domain of kinase-dead DLK (K152A) | ILDLQWVGSGAQGAVFLGRFHGEEVAVAKVRDLKETDI KHLRKLKHPNIITFKGVCTQAPCYCILMEFCAQGQLYEV LRAGRPVTPSLLVDWSMGIAGGMNYLHLHKIIHRDLKSP NMLITYDDVVKISDFGTSKELSDKSTKMSFAGTVAWMA PEVIRNEPVSEKVDIWSFGVVLWELLTGEIPYKDVDSSAII WGVGSNSLHLPVPSSCPDGFKILLRQCWNSKPRNRPSFR QILLHLDI | 8 |
| Zipper1 | REEVXLXFEKIYSEGTCLXRXEEELXMX X = E or D Y = R, H, or K | 9 |
| Zipper2 | YMELNALMLQLELYERELXRXEQALERR X = E or D Y = R, H, or K | 10 |
| Bridge | RREELRHALDIREHYERKLERANNL | 11 |
| Zipper1 - K391D, H393D | REEVDLDFEKIYSEGTCLXRXEEELXMX X = E or D Y = R, H, or K | 12 |
| Zipper1 - K391E, H393D | REEVELDFEKIYSEGTCLXRXEEELXMX X = E or D Y = R, H, or K | 13 |
| Zipper1 - K391D, H393E | REEVDLEFEKIYSEGTCLXRXEEELXMX X = E or D Y = R, H, or K | 14 |
| Zipper1 - K391E, H393E | REEVELEFEKIYSEGTCLXRXEEELXMX X = E or D Y = R, H, or K | 15 |

TABLE 2

Exemplary Polynucleotide Sequences

| Sequence description | Sequence | SEQ ID NO |
|---|---|---|
| Zipper-bridge-zipper of native DLK | GTAAAACTGCACTTTGAAAAGATTAAGTCAGAAGGGA CCTGTCTGCACCGCCTAGAAGAGGAACTGGTGATGAG GAGGAGGGAGGAGCTCAGACACGCCCTGGACATCAG GGAGCACTATGAAAGGAAGCTGGAGAGAGCCAACAA CCTGTATATGGAACTTAATGCCCTCATGTTGCAGCTGG AACTCAAGGAGAGGGAGCTGCTCAGGCGAGAGCAAG CTTTA | 16 |

TABLE 2-continued

Exemplary Polynucleotide Sequences

| Sequence description | Sequence | SEQ ID NO |
|---|---|---|
| Zipper-bridge-zipper of native DLK with flanking sequence | CTCTCCACACCCCAGGAGACTTACTTTAAGTCCCAGGC AGAGTGGCGGGAAGAAGTAAAACTGCACTTTGAAAA GATTAAGTCAGAAGGGACCTGTCTGCACCGCCTAGAA GAGGAACTGGTGATGAGGAGGAGGGAGGAGCTCAGA CACGCCCTGGACATCAGGGAGCACTATGAAAGGAAGC TGGAGAGAGCCAACAACCTGTATATGGAACTTAATGC CCTCATGTTGCAGCTGGAACTCAAGGAGAGGGAGCTG CTCAGGCGAGAGCAAGCTTTAGAGCGGAGGTGCCCAG GCCTGCTGAAGCCACACCCTTCCCGGGGCCTCCTGCA TGGAAACACAATGGAG | 17 |
| Zipper-bridge-zipper of native DLK with flanking sequence with codons corresponding to substituted bases in bold for K391E and H393E | CTCTCCACACCCCAGGAGACTTACTTTAAGTCCCAGGC AGAGTGGCGGGAAGAAGTAGAACTGGAATTTGAAAA GATTAAGTCAGAAGGGACCTGTCTGCACCGCCTAGAA GAGGAACTGGTGATGAGGAGGAGGGAGGAGCTCAGA CACGCCCTGGACATCAGGGAGCACTATGAAAGGAAGC TGGAGAGAGCCAACAACCTGTATATGGAACTTAATGC CCTCATGTTGCAGCTGGAACTCAAGGAGAGGGAGCTG CTCAGGCGAGAGCAAGCTTTAGAGCGGAGGTGCCCAG GCCTGCTGAAGCCACACCCTTCCCGGGGCCTCCTGCA TGGAAACACAATGGAG | 18 |
| Zipper-bridge-zipper of native DLK with flanking sequence with codons corresponding to substituted bases in bold for K391E, H393E, K398R, H405E, L407E, V412E, R414E, K453R, L458E, R460E | CTCTCCACACCCCAGGAGACTTACTTTAAGTCCCAGGC AGAGTGGCGGGAAGAAGTAGAACTGGAATTTGAAAA GATTCGTTCAGAAGGGACCTGTCTGCGAACGCGAAGA AGAGGAACTGGAAATGGAAAGGAGGGAGGAGCTCAG ACACGCCCTGGACATCAGGGAGCACTATGAAAGGAA GCTGGAGAGAGCCAACAACCTGTATATGGAACTTAAT GCCCTCATGTTGCAGCTGGAACTCCGTGAGAGGGAGC TGGAAAGGGAAGAGCAAGCTTTAGAGCGGAGGTGCC CAGGCCTGCTGAAGCCACACCCTTCCCGGGGCCTCCT GCATGGAAACACAATGGAG | 19 |
| Above sequence with Kozak and stop codon | GCCGCCATGGCGCTCTCCACACCCCAGGAGACTTACT TTAAGTCCCAGGCAGAGTGGCGGGAAGAAGTAGAACT GGAATTTGAAAAGATTCGTTCAGAAGGGACCTGTCTG GAACGCGAAGAAGAGGAACTGGAAATGGAAAGGAGG GAGGAGCTCAGACACGCCCTGGACATCAGGGAGCACT ATGAAAGGAAGCTGGAGAGAGCCAACAACCTGTATAT GGAACTTAATGCCCTCATGTTGCAGCTGGAACTCCGT GAGAGGGAGCTGGAAAGGGAAGAGCAAGCTTTAGAG CGGAGGTGCCCAGGCCTGCTGAAGCCACACCCTTCCC GGGGCCTCCTGCATGGAAACACAATGGAGTAA | 20 |
| Expression cassette including above sequence with Cbh promoter, hybrid intron, bGH polyA tail, and WPRE | CGTTACATAACTTACGGTAAATGGCCCGCCTGGCTGA CCGCCCAACGACCCCCGCCCATTGACGTCAATAATGA CGTATGTTCCCATAGTAACGCCAATAGGGACTTTCCAT TGACGTCAATGGGTGGAGTATTTACGGTAAACTGCCC ACTTGGCAGTACATCAAGTGTATCATATGCCAAGTAC GCCCCCTATTGACGTCAATGACGGTAAATGGCCCGCC TGGCATTATGCCCAGTACATGACCTTATGGGACTTTCC TACTTGGCAGTACATCTACGTATTAGTCATCGCTATTA CCATGGTCGAGGTGAGCCCCACGTTCTGCTTCACTCTC CCCATCTCCCCCCCCTCCCCACCCCCAATTTTGTATTT ATTTATTTTTTAATTATTTTGTGCAGCGATGGGGGCGG GGGGGGGGGGGCGGGGCGAGGGGCGGGGCGGG GCGAGGCGGAGAGGTGCGGCGGCAGCCAATCAGAGC GGCGCGCTCCGAAAGTTTCCTTTTATGGCGAGGCGGC GGCGGCGGCGGCCCTATAAAAAGCGAAGCGCGCGGC GGGCGGGAGTCGCTGCGACGCTGCCTTCGCCCCGTGC CCCGCTCCGCCGCCGCCTCGCGCCGCCCGCCCCGGCT CTGACTGACCGCGTTACTCCCACAGGTGAGCGGGCGG GACGGCCCTTCTCCTCCGGGCTGTAATTAGCGCTTGGT TTAATGACGGCTTGTTTCTTTTCTGTGGCTGCGTGAAA GCCTTGAGGGGCTCCGGGAGGGCCCTTTGTGCGGGGG |  21 |

TABLE 2-continued

Exemplary Polynucleotide Sequences

| Sequence description | Sequence | SEQ ID NO |
|---|---|---|
| | GAGCGGCTCGGGGGGTGCGTGCGTGTGTGTGCGTG<br>GGGGAGCGCCGCGTGCGGCTCCGCGCTGCCCGGCGGCT<br>GTGAGCGCTGCGGGCGCGGCGCGGGGCTTTGTGCGCT<br>CCGCAGTGTGCGCGAGGGGAGCGCGGCCGGGGGCGG<br>TGCCCCGCGGTGCGGGGGGGGCTGCGAGGGGAACAA<br>AGGCTGCGTGCGGGGTGTGTGCGTGGGGGGGTGAGCA<br>GGGGGTGTGGGCGCGTCGGTCGGGCTGCAACCCCCCC<br>TGCACCCCCCTCCCCGAGTTGCTGAGCACGGCCCGGC<br>TTCGGGTGCGGGGCTCCGTACGGGCGTGGCGCGGGG<br>CTCGCCGTGCCGGGCGGGGGTGGCGGCAGGTGGGG<br>GTGCCGGGCGGGGCGGGGCCGCCTCGGGCCGGGGAG<br>GGCTCGGGGGAGGGGCGCGGCGGCCCCCGGAGCGCC<br>GGCGGCTGTCGAGGCGCGGCGAGCCGCAGCCATTGCC<br>TTTTATGGTAATCGTGCGAGAGGGCGCAGGGACTTCC<br>TTTGTCCCAAATCTGTGCGGAGCCGAAATCTGGGAGG<br>CGCCGCCGCACCCCCTCTAGCGGGCGCGGGGCGAAGC<br>GGTGCGGCGCCGGCAGGAAGGAAATGGGCGGGGAGG<br>GCCTTCGTGCGTCGCCGCGCCGCCGTCCCCTTCTCCCT<br>CTCCAGCCTCGGGGCTGTCCGCGGGGGGACGGCTGCC<br>TTCGGGGGGACGGGGCAGGGCGGGGTTCGGCTTCTG<br>GCGTGTGACCGGCGGCTCTAGAGCCTCTGCTAACCAT<br>GTTCATGCCTTCTTCTTTTTCCTACAGCTCCTGGGCAA<br>CGTGCTGGTTATTGTGCTGTCTCATCATTTTGGCAAAG<br>AATTCGAGCGGCCGCCAGTGTGAGTTGGACCGGTGCC<br>GCCATGGCGCTCTCCACACCCCAGGAGACTTACTTTA<br>AGTCCCAGGCAGAGTGGCGGGAAGAAGTAGAACTGG<br>AATTTGAAAAGATTCGTTCAGAAGGGACCTGTCTGGA<br>ACGCGAAGAAGAGGAACTGGAAATGGAAAGGAGGGA<br>GGAGCTCAGACACGCCCTGGACATCAGGGAGCACTAT<br>GAAAGGAAGCTGGAGAGAGCCAACAACCTGTATATG<br>GAACTTAATGCCCTCATGTTGCAGCTGGAACTCCGTG<br>AGAGGGAGCTGGAAAGGGAAGAGCAAGCTTTAGAGC<br>GGAGGTGCCCAGGCCTGCTGAAGCCACACCCTTCCCG<br>GGGCCTCCTGCATGGAAACACAATGGAGTAATGAGGC<br>ATGCTTCTATATTATTTTCTAAAAGATTTAAAGTTTTG<br>CCTTCTCCATTTAGACTTATAATTCACTGGAATTTTTTT<br>GTGTGTATGGTATGACATATGGGTTCCCTTTTATTTTTT<br>ACATATAAATATATTTCCCTGTTTTTCTAAAAAAGACC<br>TAGGAAAACTGTCTTCATAATCAACCTCTGGATTACA<br>AAATTTGTGAAAGATTGACTGGTATTCTTAACTATGTT<br>GCTCCTTTTACGCTATGTGGATACGCTGCTTTAATGCC<br>TTTGTATCATGCTATTGCTTCCCGTATGGCTTTCATTTT<br>CTCCTCCTTGTATAAATCCTGGTTGCTGTCTCTTTATGA<br>GGAGTTGTGGCCCGTTGTCAGGCAACGTGGCGTGGTG<br>TGCACTGTGTTTGCTGACGCAACCCCCACTGGTTGGGG<br>CATTGCCACCACCTGTCAGCTCCTTTCCGGGACTTTCG<br>CTTTCCCCCTCCCTATTGCCACGGCGGAACTCATCGCC<br>GCCTGCCTTGCCCGCTGCTGGACAGGGGCTCGGCTGTT<br>GGGCACTGACAATTCCGTGGTGTTGTCGGGGAAATCA<br>TCGTCCTTTCCTTGGCTGCTCGCCTATGTTGCCACCTG<br>GATTCTGCGCGGGACGTCCTTCTGCTACGTCCCTTCGG<br>CCCTCAATCCAGCGGACCTTCCTTCCCGCGGCCTGCTG<br>CCGGCTCTGCGGCCTCTTCCGCGTCTTCGCCTTCGCCC<br>TCAGACGAGTCGGATCTCCCTTTGGGCCGCCTCCCCGC<br>ATCGATACCGAGCGCTGCTAGAGAGATCGATCTGCCT<br>CAACTGTGCCTTCTAGTTGCCAGCCATCTGTTGTTTGC<br>CCCTCCCCCGTGCCTTCCTTGACCCTGGAAGGTGCCAC<br>TCCCACTGTCCTTTCCTAATAAAATGAGGAAATTGCAT<br>CGCATTGTCTGAGTAGGTGTCATTCTATTCTGGGGGGT<br>GGGGTGGGGCAGGACAGCAAGGGGGAGGATTGGGAA<br>GAGAATAGCAGGCATGCTGGGGATGCGGTGGGCTCTA<br>TGGGTACCCAGGTGCTGAAGAATTGACCCGGTTCCTC<br>CTGGG | |
| Expression cassette above with flanking AAV ITRs | ATGTCCTACAGCGCGCTCGCTCGCTCACTGAGGCCGC<br>CCGGGCAAAGCCCGGGCGTCGGGCGACCTTTGGTCGC<br>CCGGCCTCAGTGAGCGAGCGAGCGCGCAGAGAGGGA<br>GTGGCCAACTCCATCACTAGGGGTTCCTTGTAGTTAAT<br>GATTAACCTCTGGAGACCGCCATGCTACTTATCTACCA<br>GGGTAATGGGATCCTCTAGAACTATAGCGTTACATA<br>ACTTACGGTAAATGGCCCGCCTGGCTGACCGCCCAAC | 22 |

TABLE 2-continued

Exemplary Polynucleotide Sequences

| Sequence description | Sequence | SEQ ID NO |
|---|---|---|
| | GACCCCCGCCCATTGACGTCAATAATGACGTATGTTCC | |
| | CATAGTAACGCCAATAGGGACTTTCCATTGACGTCAA | |
| | TGGGTGGAGTATTTACGGTAAACTGCCCACTTGGCAG | |
| | TACATCAAGTGTATCATATGCCAAGTACGCCCCCTATT | |
| | GACGTCAATGACGGTAAATGGCCCGCCTGGCATTATG | |
| | CCCAGTACATGACCTTATGGGACTTTCCTACTTGGCAG | |
| | TACATCTACGTATTAGTCATCGCTATTACCATGGTCGA | |
| | GGTGAGCCCCACGTTCTGCTTCACTCTCCCCATCTCCC | |
| | CCCCCTCCCCACCCCCAATTTTGTATTTATTTATTTTT | |
| | AATTATTTTGTGCAGCGATGGGGGCGGGGGGGGGGG | |
| | GGGGCGGGGCGAGGGGCGGGGCGGGGCGAGGCGGAG | |
| | AGGTGCGGCGGCAGCCAATCAGAGCGGCGCGCTCCGA | |
| | AAGTTTCCTTTTATGGCGAGGCGGCGGCGGCGGCGGC | |
| | CCTATAAAAAGCGAAGCGCGCGGCGGGCGGGAGTCG | |
| | CTGCGACGCTGCCTTCGCCCCGTGCCCGCTCCGCCGC | |
| | CGCCTCGCGCCGCCCGCCCCGGCTCTGACTGACCGCG | |
| | TTACTCCCACAGGTGAGCGGGCGGGACGGCCCTTCTC | |
| | CTCCGGGCTGTAATTAGCGCTTGGTTTAATGACGGCTT | |
| | GTTTCTTTTCTGTGGCTGCGTGAAAGCCTTGAGGGGCT | |
| | CCGGGAGGGCCCTTTGTGCGGGGGGAGCGGCTCGGGG | |
| | GGTGCGTGCGTGTGTGTGTGCGTGGGGAGCGCCGCGT | |
| | GCGGCTCCGCGCTGCCCGGCGGCTGTGAGCGCTGCGG | |
| | GCGCGGCGCGGGCTTTGTGCGCTCCGCAGTGTGCGC | |
| | GAGGGGAGCGCGGCCGGGGCGGTGCCCCGCGGTGC | |
| | GGGGGGGGCTGCGAGGGGAACAAAGGCTGCGTGCGG | |
| | GGTGTGTGCGTGGGGGGGTGAGCAGGGGGTGTGGGC | |
| | GCGTCGGTCGGGCTGCAACCCCCCCTGCACCCCCCTC | |
| | CCCGAGTTGCTGAGCACGGCCCGGCTTCGGGTGCGGG | |
| | GCTCCGTACGGGGCGTGGCGCGGGGCTCGCCGTGCCG | |
| | GGCGGGGGTGGCGGCAGGTGGGGGTGCCGGGCGGG | |
| | GCGGGGCCGCCTCGGGCCGGGGAGGGCTCGGGGGAG | |
| | GGGCGCGGCGGCCCCCGGAGCGCCGGCGGCTGTCGA | |
| | GGCGCGGCGAGCCGCAGCCATTGCCTTTTATGGTAAT | |
| | CGTGCGAGAGGGCGCAGGGACTTCCTTTGTCCCAAAT | |
| | CTGTGCGGAGCCGAAATCTGGGAGGCGCCGCCGCACC | |
| | CCCTCTAGCGGGCGCGGGGCGAAGCGGTGCGGCGCCG | |
| | GCAGGAAGGAAATGGGCGGGGAGGGCCTTCGTGCGT | |
| | CGCCGCGCCGCCGTCCCCTTCTCCCTCTCCAGCCTCGG | |
| | GGCTGTCCGCGGGGGGACGGCTGCCTTCGGGGGGGAC | |
| | GGGGCAGGGCGGGGTTCGGCTTCTGGCGTGTGACCGG | |
| | CGGCTCTAGAGCCTCTGCTAACCATGTTCATGCCTTCT | |
| | TCTTTTTCCTACAGCTCCTGGGCAACGTGCTGGTTATT | |
| | GTGCTGTCTCATCATTTTGGCAAAGAATTCGAGCGGCC | |
| | GCCAGTGTGAGTTGGACCGGTGCCGCCATGGCGCTCT | |
| | CCACACCCCAGGAGACTTACTTTAAGTCCCAGGCAGA | |
| | GTGGCGGGAAGAAGTAGAACTGGAATTTGAAAAGATT | |
| | CGTTCAGAAGGGACCTGTCTGGAACGCGAAGAAGAG | |
| | GAACTGGAAATGGAAAGGAGGGAGGAGCTCAGACAC | |
| | GCCCTGGACATCAGGGAGCACTATGAAAGGAAGCTGG | |
| | AGAGAGCCAACAACCTGTATATGGAACTTAATGCCCT | |
| | CATGTTGCAGCTGGAACTCCGTGAGAGGGAGCTGGAA | |
| | AGGGAAGAGCAAGCTTTAGAGCGGAGGTGCCCAGGC | |
| | CTGCTGAAGCCACACCCTTCCCGGGGCCTCCTGCATG | |
| | GAAACACAATGGAGTAATGAGGCATGCTTCTATATTA | |
| | TTTTCTAAAAGATTTAAAGTTTTGCCTTCTCCATTTAG | |
| | ACTTATAATTCACTGGAATTTTTTTGTGTGTATGGTAT | |
| | GACATATGGGTTCCCTTTTATTTTTTACATATAAATAT | |
| | ATTTCCCTGTTTTTCTAAAAAAGACCTAGGAAAACTGT | |
| | CTTCATAATCAACCTCTGGATTACAAAATTTGTGAAAG | |
| | ATTGACTGGTATTCTTAACTATGTTGCTCCTTTTACGCT | |
| | ATGTGGATACGCTGCTTTAATGCCTTTGTATCATGCTA | |
| | TTGCTTCCCGTATGGCTTTCATTTTCTCCTCCTTGTATA | |
| | AATCCTGGTTGCTGTCTCTTTATGAGGAGTTGTGGCCC | |

TABLE 2-continued

Exemplary Polynucleotide Sequences

| Sequence description | Sequence | SEQ ID NO |
|---|---|---|
| | GTTGTCAGGCAACGTGGCGTGGTGTGCACTGTGTTTGC TGACGCAACCCCCACTGGTTGGGGCATTGCCACCACC TGTCAGCTCCTTTCCGGGACTTTCGCTTTCCCCCTCCCT ATTGCCACGGCGGAACTCATCGCCGCCTGCCTTGCCC GCTGCTGGACAGGGGCTCGGCTGTTGGGCACTGACAA TTCCGTGGTGTTGTCGGGGAAATCATCGTCCTTTCCTT GGCTGCTCGCCTATGTTGCCACCTGGATTCTGCGCGGG ACGTCCTTCTGCTACGTCCCTTCGGCCCTCAATCCAGC GGACCTTCCTTCCCGCGGCCTGCTGCCGGCTCTGCGGC CTCTTCCGCGTCTTCGCCTTCGCCCTCAGACGAGTCGG ATCTCCCTTTGGGCCGCCTCCCCGCATCGATACCGAGC GCTGCTAGAGAGATCGATCTGCCTCAACTGTGCCTTCT AGTTGCCAGCCATCTGTTGTTTGCCCCTCCCCCGTGCC TTCCTTGACCCTGGAAGGTGCCACTCCCACTGTCCTTT CCTAATAAAATGAGGAAATTGCATCGCATTGTCTGAG TAGGTGTCATTCTATTCTGGGGGGTGGGGTGGGGCAG GACAGCAAGGGGGAGGATTGGGAAGAGAATAGCAGG CATGCTGGGGATGCGGTGGGCTCTATGGGTACCCAGG TGCTGAAGAATTGACCCGGTTCCTCCTGGGGAAGCAA TTCGTTGATCTGAATTTCGACCACCGATAATACCTATT ACCCTGGTAGATAAGTAGCACGGCGGGTTAATGATTA ACTACAGCAATTCGTTGATCTGAATTTCGACCACCCAT AATAGATCTCCCATTACCCTGGTAGATAAGTAGCATG GCGGGACAATTAAGTACCTCAAAGAACTATTCTTGTTT GCCTTATTCCTATGTAAATAACTGAAATCTTTGTTTTT CTTCCTAAAAGGGGTGATGTTGATTTTTACTTACAATG TATTTTAAGTTTGTCACTCTAAATGGTTATGAGCAAGT TTAAGAAAAATCTTCAGCAAATACTACCTTAGATTAT GACCCCAAAACACATTTACTTATGATTATGTTGAAAA CATAGGGTCTGGGGAAAAAGGGATTTAAATTAAGAAG AAAAAGAAGACTTCGGACTTAAAAAGTCTTTTAGAGG CCAGCTCACCAACAACACAACACCGAGTCTGTGTTGC ACAATATGTTACTTAGGTATAAATCAAGGATTCATGT AATTTTGTCATTCCTTGCGTGATATTTTAAAAAACATT CTGTGTAAGGTATTTATAAAGCTCTCTTCTAAAAATAC AAAAATTTGTGTCATTAATCAACAGTCAGGTTAATCAT TAACTACAAGGAACCCCTAGTGATGGAGTTGGCCACT CCCTCTCTGCGCGCTCGCTCGCTCACTGAGGCCGGGC GACCAAAGGTCGCCCGACGCCCGGGCTTTGCCCGGGC GGCCTCAGTGAGCGAGCGAGCGCGCACTGTCA | 40 |

It has been shown the DLK is a target for at least one microRNA, miR-130a. Ye et al. MicroRNA-130a Targets MAP3K12 to Modulate Diabetic Endothelial Progenitor Cell Function. *Cell Physiol Biochem*. 2015; 36(2):712-26 (2015). Other examples of microRNA inhibitors of DLK are hsa-miR-10a-3p, hsa-miR-155-5p, and hsa-miR-30a-5p. Hu et al. *Oncology Lett*. 15:467-474 (2018). In some embodiments the inhibitor comprises a microRNA from Table 3 or a functional equivalent thereof.

TABLE 3

Exemplary microRNA sequences

| Sequence description | Sequence | miRBase Accession | SEQ ID NO |
|---|---|---|---|
| hsa-mir-130a | UGCUGCUGGCCAGAGCUCUUUUCAC AUUGUGCUACUGUCUGCACCUGUCA CUAGCAGUGCAAUGUUAAAAGGGC AUUGGCCGUGUAGUG | MI0000448 | 19 |
| hsa-miR-10a-5p | UACCCUGUAGAUCCGAAUUUGUG | MIMAT0000253 | 20 |
| hsa-miR-155-5p | UUAAUGCUAAUCGUGAUAGGGGUU | MIMAT0000646 | 21 |
| hsa-mir-30a | GCGACUGUAAACAUCCUCGACUGGA AGCUGUGAAGCCACAGAUGGGCUU UCAGUCGGAUGUUUGCAGCUGC | MI0000088 | 22 |

3.5 In Vivo and In Vitro Assays

The present disclosure further relates to assessment of efficacy and safety of gene therapy vectors in in vitro assay systems. Expression levels can be measured by immunohistochemistry of target cells or tissues. In some embodiments the vectors of the disclosure comprise nucleic acids encoding fluorescent proteins or other marker proteins used to assess transduction efficiency or gene expression levels. Functional assays include standard test of vision as well as inspection of the subjects' eye.

3.6 Therapeutic Compositions and Methods

As used herein, the term "patient in need" or "subject in need" refers to a patient or subject at risk of, or suffering from, a disease, disorder or condition that is amenable to treatment or amelioration with a vector as provided herein. A patient or subject in need may, for instance, be a patient or subject diagnosed with a disease associated retinal cells. "Subject" and "patient" are used interchangeably herein.

The subject treated by the methods described herein may be a mammal. In some cases, a subject is a human, a non-human primate, a pig, a horse, a cow, a dog, a cat, a rabbit, a mouse or a rat. A subject may be a human female or a human male. Subjects may range in age. Thus, the present disclosure contemplates administering any of the vectors of the disclosure to a subject suffering optic neuropathy.

Combination therapies are also contemplated by the invention. Combination as used herein includes simultaneous treatment or sequential treatment. Combinations of methods of the invention with standard medical treatments (e.g., corticosteroids or topical pressure reducing medications) are specifically contemplated, as are combinations with novel therapies. In some cases, a subject may be treated with a steroid to prevent or to reduce an immune response to administration of a vector described herein. In certain cases, a subject may receive topical pressure reducing medications before, during, or after administrating of a vector described herein. In certain cases, a subject may receive a medication capable of causing the pupil of the eye to dilate (e.g., tropicamide and/or phenylephrine). In certain cases, the subject may receive a moisturizing gel during recovery to prevent corneal dehydration.

A therapeutically effective amount of the rAAV vector is a dose of rAAV ranging from about 1e8 to about 1e13 vector genomes (vg), more specifically 1e10-1e12 vg or 1e11 vg.

In some cases, the therapeutic composition comprises more than about 1e9, 1e10, or 1e11 genomes of the rAAV vector per volume of therapeutic composition injected. In some cases, the therapeutic composition comprises more than approximately 1e10, 1e11, 1e12, or 1e13 genomes of the rAAV vector per mL.

3.7 Administration of Compositions

Administration of an effective dose of the compositions may be by routes standard in the art including, but not limited to, intracameral inoculation, intravitreal inoculation, subretinal inoculation, suprachoroidal inoculation, canaloplasty, or episcleral vein-mediated delivery. Route(s) of administration and serotype(s) of AAV components of the rAAV (in particular, the AAV ITRs and capsid protein) of the invention may be chosen and/or matched by those skilled in the art taking into account the disease state being treated and the target cells/tissue(s).

The disclosure provides for local administration and systemic administration of an effective dose of rAAV and compositions of the invention. For example, systemic administration is administration into the circulatory system so that the entire body is affected. Systemic administration includes enteral administration such as absorption through the gastrointestinal tract and parental administration through injection, infusion or implantation or intravenous administration.

In particular, actual administration of rAAV of the present invention may be accomplished by using any physical method that will transport the rAAV recombinant vector into the target tissue of an animal. Administration according to the invention includes, but is not limited to, injection into the bloodstream and/or directly into the eye. Simply resuspending arAAV in phosphate buffered saline has been demonstrated to be sufficient to provide a vehicle useful for eye expression, and there are no known restrictions on the carriers or other components that can be co-administered with the rAAV (although compositions that degrade DNA should be avoided in the normal manner with rAAV).

Capsid proteins of a rAAV may be modified so that the rAAV is targeted to a particular target tissue of interest such as eye. See, for example, WO 02/053703, the disclosure of which is incorporated by reference herein. Pharmaceutical compositions can be prepared as injectable formulations or as topical formulations to be delivered to the eyes by administration of eye drops or otherwise. Additionally, when a tetracycline-inducible promoter is used to control transgene expression, it may be advantageous to co-administer doxycycline via eyedrops. Numerous formulations of rAAV have been previously developed and can be used in the practice of the invention. The rAAV can be used with any pharmaceutically acceptable carrier for ease of administration and handling.

For purposes of injection, various solutions can be employed, such as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target cells are removed from the subject, transduced with rAAV and reintroduced into the subject. Alternatively, syngeneic or xenogeneic ocular cells can be used where those cells will not generate an inappropriate immune response in the subject.

Suitable methods for the transduction and reintroduction of transduced cells into a subject are known in the art. In one embodiment, cells can be transduced in vitro by combining rAAV with cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intracameral inoculation, intravitreal inoculation, subretinal inoculation, canaloplasty, intrathecal delivery, sterotactic delivery to brain, or episcleral vein-mediated delivery. In some embodiments, transduction of cells with rAAV of the invention results in sustained expression of the inhibitor of DLK for more than 1 month, more than 2 months, more than 3 months, more than 4 months, more than 5 months, more than 6 months, more than 9 months, or more than 12 months. The present invention thus provides methods of administering/delivering rAAV which express an inhibitor of DLK to a mammalian subject, preferably a human being. These methods include transducing tissues (including the tissues of the eye, motor neurons, or brain) with one or more rAAV of the present invention. Transduction may be carried out with gene cassettes comprising tissue specific control elements. For example, one embodiment of the invention provides methods of transducing eye cells and eye tissues directed by eye specific control elements, including promoters described herein.

4.1 Inhibitors

In some embodiments, the disclosure provides an inhibitor, comprising a protein comprising a leucine zipper domain that shares at least 95% identity to SEQ ID NO: 3, wherein the leucine zipper domain comprises at least one or at least two substitutions at positions 391 and 393, relative to SEQ ID NO: 1. In some embodiments, said substitutions comprise K391 to D or K391 to E, and H393 to D or H393 to E. In some embodiments, said substitutions, individually or collectively, either (i) increase the binding affinity of the leucine zipper domain for endogenous DLK or (ii) decrease affinity of said inhibitor for itself, compared to the corresponding protein without said substitutions.

In some embodiments, the leucine zipper domain further comprises one or more additional substitutions at one or more positions, related to SEQ ID NO: 1 selected from one or more of K398, L407, H405, V412, R414, K453, L458, and R460. In some embodiments, the one or more substations comprise K398 to R if the one or more positions comprise K398; L407 to D or L407 to E if the one or more positions comprise L407; H405 to D or H405 to E if the one or more positions comprise H405; V412 to D or V412 to E if the one or more positions comprise V412; R414 to D or R414 to E if the one or more positions comprise R414; K453 to R if the one or more positions comprise K453; L458 to D or L458 to E if the one or more positions comprise L458; and R460 to D or R460 to E if the one or more positions comprise R460.

In some embodiments, the inhibitory domain comprises, in N terminal to C terminal order a first polypeptide having sequence REEVXLXFEKIYSEGTCLXRXEEELXMX (SEQ ID NO: 9); a polypeptide bridge comprising 20 to 30 amino-acid residues, optionally SEQ ID NO: 11; and a second polypeptide having sequence YMELNALMLQLELYERELXR XEQALERR (SEQ ID NO: 10); wherein X=E or D and Y=R, H, or K.

In some embodiments, the first polypeptide is selected from the group consisting of a polypeptide having sequence REEVDLDFEKIYSEGTCLXRXEEELXMX (SEQ ID NO: 12); a polypeptide having sequence REEVELDFEKIY-SEGTCLXRXEEELXMX (SEQ ID NO: 13); a polypeptide having sequence REEVDLEFEKIYSEGT-CLXRXEEELXMX (SEQ ID NO: 14); and a polypeptide having sequence REEVELEFEKIYSEGT-CLXRXEEELXMX (SEQ ID NO: 15); wherein X=E or D and Y=R, H, or K.

In some embodiments, the leucine zipper domain comprises a polypeptide that shares at least 75%, at least 80%, at least 85%, at least 90%, at least 95%, at least 99%, or 100% identity to one of SEQ ID NO: 6 or SEQ ID NO: 7. In some embodiments, the leucine zipper domain comprises a polypeptide identical to one of SEQ ID NO: 6 or SEQ ID NO: 7. In some embodiments, the substitution either (i) increases affinity of the leucine zipper domain for endogenous DLK, or (ii) decreases affinity of the leucine zipper domain for itself; each of (i) and (ii) as compared to the same leucine zipper domain having the native residue at the position of the substitution. In some embodiments, the leucine zipper preferentially forms heterodimers with endogenous DLK compared to either one of (i) homodimers of the inhibitor or (ii) DLK homodimers.

In some embodiments, the inhibitor comprises a DLK kinase domain having at least 95% identity to SEQ ID NO: 5, wherein the DLK kinase domain comprises a substitution that decreases the kinase activity of the DLK kinase domain. In some embodiments, the substitution that decreases the kinase activity of the DLK kinase domain is a substitution of lysine (K) at position 152 relative to SEQ ID NO: 1, from lysine (K) to alanine (A). In some embodiments, the DLK kinase domain comprises SEQ ID NO. 8.

In some embodiments, the inhibitor comprises a functional fragment of LZK. In some embodiments, the inhibitor comprises a functional fragment a neurotrophic factor, optionally BDNF, GDNF, NT4, TrkB, RdCVF, or CNTF, or a functional fragment thereof. In some embodiments, the inhibitor further comprises a functional fragment capable of inhibiting CAMP-mediated signaling, optionally cAMP-mediated signalling through mAKAP. In some embodiments, the inhibitor comprises a second domain, and the inhibitor is capable of having neurotrophic activity in the cell.

4.2 Vectors

The disclosure provides a vector, comprising a polynucleotide encoding an inhibitor of Dual Leucine Zipper Kinase (DLK), the polynucleotide operatively linked to a promoter, wherein the inhibitor is capable of binding either (i) an endogenous DLK protein, or (ii) an endogenous mRNA encoding an endogenous DLK; and wherein the inhibitor is capable of reducing the expression, signaling activity, or kinase activity of the endogenous DLK in a retinal cell. As already stated, the vector may be viral or non-viral. In some embodiments, the vector is recombinant AAV.

In some embodiments, the promoter is a ubiquitous promoter. As used herein a "ubiquitous promoter" is a promoter that is capable of mediating expression of a polynucleotide in many, if not most, cells of a target organism. Generally ubiquitous promoters in one eukaryotic organism are capable of mediating expression in others. Ubiquitous promoters include mammalian promoters. In some embodiments, the ubiquitous promoter comprises a CMV promoter, a CAG promoter, CBA promoter, or a CBh promoter. In some embodiments, the promoter is a retinal cell-type specific. In some embodiments, the promoter is an RGC-specific promoter. Exemplary RGC-specific promoters, e.g. the Nefh promoter, are provided by Hanlon et al. *Front Neurosci.* 2017 Sep. 21; 11:521.

In some embodiments, the promoter is a Thy1 promoter, a Nefh promoter, or a DCX promoter. The DCX promoter is described in Smith et al. *Sci Rep.* 8:1490 (2018); and US20140248701A1. In some embodiments, the promoter is a minipromoter. In some embodiments, said minipromoter is derived from POU4F1, TUBB3, NEFL, or NEFM. The NEFL promoter is described in Simpson et al. New Mini-Promoter Ple345 (NEFL) Drives Strong and Specific Expression in Retinal Ganglion Cells of Mouse and Primate Retina. *Hum Gene Ther.* (2018). In some embodiments, the promoter is a rod photoreceptor-specific promoter. In some embodiments, the promoter is a rhodopsin promoter or an RK promoter. In some embodiments, the promoter is a cone photoreceptor-specific promoter. In some embodiments, the promoter is a pR2.1 promoter or a MNTC promoter, as disclosed in U.S. Pat. No. 10,000,741, which is incorporated here in its entirety.

In some embodiments, the inhibitor is an RNA capable of binding an endogenous mRNA encoding an endogenous DLK, and wherein the inhibitor is capable of reducing the expression of the endogenous DLK in the cell. In some embodiments, the inhibitor is an shRNA or an siRNA. In some embodiments, the inhibitor is a microRNA. In some embodiments, the microRNA is miR-130a, miR-122-5p, miR-30a-5p, or miR-10-3p. In some embodiments, inhibitor is a protein capable of binding an endogenous DLK, and In some embodiments, wherein the inhibitor is capable of reducing the signaling activity or the kinase activity of the endogenous DLK in the cell.

In some embodiments, the protein comprises an inhibitory domain, the inhibitory domain comprising a leucine zipper domain. In some embodiments, the inhibitory domain is capable of binding the leucine zipper domain of endogenous DLK, thereby competitively inhibiting homodimerization of said endogenous DLK or competitively inhibiting heterodimerization of said endogenous DLK and endogenous Leucine Zipper Kinase (LZK). In some embodiments, the inhibitory domain comprises, consists essentially of, or consists of a polypeptide at least 75%, at least 80%, at least 85%, at least 90%, at least 95%, at least 99%, or 100% identical to SEQ ID NO: 3 or SEQ ID NO: 4.

In some embodiments, the leucine zipper domain of the inhibitory domain comprises at least one amino acid substitution relative to SEQ ID NO: 1, and In some embodiments, wherein the substitution increases affinity of the leucine zipper domain for endogenous DLK or decreases affinity of the leucine zipper domain for itself. In some embodiments, the inhibitory domain contains a substitution selected from those listed in Table 4.

In some embodiments, the inhibitory domain comprises, in N terminal to C terminal order, a polypeptide having sequence REEVXLXFEKIYSEGTCLXRXEEELXMX (SEQ ID NO: 9), a polypeptide bridge comprising 20, 21, 22, 23, 24, 25, 26, 27, 28, 29, or 30 amino-acid residues, optionally SEQ ID NO: 11, and a polypeptide having sequence YMELNALMLQLELYERELXRXEQALERR (SEQ ID NO: 10), wherein X=E or D and Y=R, H, or K.

In some embodiments, the inhibitory domain comprises a polypeptide that shares at least 75%, at least 80%, at least 85%, at least 90%, at least 95%, at least 99%, or 100% identity to one of SEQ ID NO: 6 or SEQ ID NO: 7. In some embodiments, the inhibitory zipper domain comprises a polypeptide that is identical to one of SEQ ID NO: 6 or SEQ ID NO: 7. In some embodiments, the substitution increases affinity of the leucine zipper domain for endogenous DLK or decreases affinity of the leucine zipper domain for itself compared to the same leucine zipper domain having the native residue at the position of the substitution. In some embodiments, the leucine zipper preferentially forms heterodimers with endogenous DLK compared to either one of (i) inhibitor homodimers or (ii) DLK homodimers.

In some embodiments, the inhibitor comprises a DLK kinase domain having at least 75% identity to SEQ ID NO: 5, wherein the DLK kinase domain comprises a substitution that decreases the kinase activity of the DLK kinase domain. In some embodiments, the inhibitor is an inactive form of DLK. In some embodiments, said inhibitor contains a substitution at position 152 relative to SEQ ID NO: 1 from lysine (K) to alanine (A). In some embodiments, the DLK kinase domain comprises SEQ ID NO: 8. In some embodiments, the inhibitor comprises a functional fragment of LZK. In some embodiments, the inhibitor comprises a functional fragment a neurotrophic factor, optionally BDNF, GDNF, NT4, TrkB, RdCVF, or CNTF, or a functional fragment thereof. In some embodiments, the inhibitor comprises a functional fragment capable of inhibiting cAMP-mediated signaling, optionally cAMP-mediated signaling through mAKAP. In some embodiments, the inhibitor comprises a second domain, and wherein the inhibitor is capable of having neurotrophic activity in the cell.

In some embodiments, the vector is a recombinant adeno-associated virus (rAAV) vector. In some embodiments, the vector is a non-viral vector.

In some embodiments, the disclosure provides, a recombinant virus vector, comprising an expression cassette comprising a polynucleotide encoding the inhibitor of claim 1 operably linked to a promoter.

In some embodiments, the virus is a recombinant adeno-associated virus (rAAV) vector. In some embodiments, the expression cassette is flanked by 5' ITR and 3' ITR. In some embodiments, the vector comprises a genome between 3.2 kb and 5.0 kb, 3.4 kb and 4.9 kb, 3.6 kb and 4.8 kb, 3.8 kb and 4.7 kb, 3.8 kb and 4.6 kb, 4.0 kb and 4.6 kb, 4.2 kb and 4.6 kb, 4.2 kb and 4.4 kb, or 4.4 kb and 4.6 kb. In some embodiments, the vector comprises a genome between 3.2 kb and 3.4 kb, 3.4 kb and 3.6 kb, 3.6 kb and 3.8 kb, 3.8 kb and 4.0 kb, 4.0 kb and 4.2 kb, 4.2 kb and 4.4 kb, 4.4 kb and 4.6 kb, 4.6 kb and 4.8 kb, or 4.8 kb and 5.0 kb. In some embodiments, the vector comprises a genome of about 3.2 kb, 3.3 kb, 3.4 kb, 3.5 kb, 3.6 kb, 3.7 kb, 3.8 kb, 3.9 kb, 4.0 kb, 4.1 kb, 4.2 kb, 4.3 kb, 4.4 kb, 4.5 kb, 4.6 kb, 4.7 kb, or 4.8 kb. In some embodiments, the rAAV comprises a deletion of one or more non-essential genes. In some embodiments, the rAAV comprises a deletion of one or more essential genes, provided in trans during production of the rAAV. In some embodiments, the rAAV comprises a deletion of rep, cap, and rep or cap. In some embodiments, the rAAV is a self-complementary AAV. In some embodiments, the rAAV comprises a deletion in the D region of either or both of the 5' ITR and 3' ITR. In some embodiments, the rAAV is a hybrid AAV. In some embodiments, the rAAV comprises a stuffer sequence. In some embodiments, the rAAV comprises the 5' ITR and 3' ITR of AAV2 and the capsid proteins of an AAV serotype other than AAV2. In some embodiments, the rAAV comprises 5' ITR and 3' ITR from different serotypes. In some embodiments the rAAV is modified by one or more of transcapsidation, adsorption modification, mosaic capsid, or chimeric capsid (e.g. as described in Choi et al. *Curr Gene Ther.* 2005 June; 5(3): 299-310).

In some embodiments, the vector comprises a capsid of serotype AAV1, AAV2, AAV4, AAV5, AAV7, AAV8, AAV9, or AAV2/2(7m8). In some embodiments, the rAAV selectively infects a cell type, such as neurons, retinal cells, or RGCs. Serotypes useful in the vectors of the present disclosure include those described in Lebherz et al. *J Gene Med.* 2008 April; 10(4): 375-382; Hanlon et al. *Front Neurosci.* 2017; 11:521; and Hickey et al. *Gene Therapy* 24:787-800 (2017).

In some embodiments, the promoter is a ubiquitous promoter. As used herein a "ubiquitous promoter" is a promoter that is capable of mediating expression of a polynucleotide in many, if not most, cells of a target organism. Generally ubiquitous promoters in one eukaryotic organism are capable of mediating expression in others. Ubiquitous promoters include mammalian promoters. In some embodiments, the ubiquitous promoter comprises a CMV promoter, a CAG promoter, CBA promoter, or a CBh promoter. In some embodiments, the promoter is a retinal cell-type specific. In some embodiments, the promoter is an RGC-specific promoter. Exemplary RGC-specific promoters, e.g. the Nefh promoter, are provided by Hanlon et al. *Front Neurosci.* 2017 Sep. 21; 11:521.

In some embodiments, the promoter is a Thy1 promoter, a Nefh promoter, or a DCX promoter. The DCS promoter is described in Smith et al. Sci Rep.8:1490 (2018); and US20140248701A1. In some embodiments, the promoter is a minipromoter. In some embodiments, said minipromoter is derived from POU4F1, TUBB3, NEFL, or NEFM. The NEFL promoter is described in Simpson et al. New Mini-Promoter Ple345 (NEFL) Drives Strong and Specific Expression in Retinal Ganglion Cells of Mouse and Primate Retina. *Hum Gene Ther.* (2018). In some embodiments, the promoter is a rod photoreceptor-specific promoter. In some embodiments, the promoter is a rhodopsin promoter or an RK promoter. In some embodiments, the promoter is a cone photoreceptor-specific promoter. In some embodiments, the promoter is a pR2.1 promoter or a MNTC promoter.

4.3 Methods of Treatment

In some embodiments, the disclosure provides a method of treating a disease or disorder, comprising contacting a cell with any of the vectors of the disclosure. In some embodiments, the cell is a retinal cell. In some embodiments, the retinal cell is a retinal ganglion cell (RGC), a photoreceptor cell, or a retinal neuron (e.g. a bipolar cell, an amacrine cell, or a horizontal cell). In some embodiments, the cell is a dopaminergic neuron, a dorsal striatum neuron, or a basal forebrain cholinergic neuron. In some embodiments, the vector is administered by injection of a volume of solution of about 10 to 100 µL, preferably 50 µL. In some embodiments, the disease or disorder is related to dysfunction in retinal cells. In some embodiments, the disease or disorder related to dysfunction in retinal cells is selected from the group consisting of glaucoma, wet macular degeneration, dry macular degeneration, geographic atrophy, retinal detachment, and retinal dystrophy, such as Usher's syndrome, Stargardt's disease, Leber's congenital amaurosis, or retinitis pigmentosa. In yet other embodiments, the disease is related to retinopathy, such as diabetic retinopathy, myopic maculopathy. In other embodiments, the disease is an optic neuropathy, such as optic neuritis, non-arteritic anterior ischemic optic neuropathy (NAION), arteritic anterior ischemic optic neuropathy (AION), traumatic optic neuropathy, Leber's optic neuropathy, dominant optic atrophy, recessive optic atrophy, or radiation optic neuropathy.

In some embodiments, the disclosure provides a method of treating a disease or disorder related to retinal cells, comprising administering to the retina of the subject any of the vectors of the disclosure. In some embodiments, the retinal cell is a retinal ganglion cell (RGC), a photoreceptor cell, or a retinal neuron—such as a bipolar cell, an amacrine cell, or a horizontal cell. In some embodiments, the vector is administered by injection of a volume of solution of about 10 to 100 µL, preferably 50 µL. In some embodiments, the disease or disorder related to dysfunction in retinal cells is selected from the group consisting of glaucoma, wet macular degeneration, dry macular degeneration, geographic atrophy, retinal detachment, and retinal dystrophy, such as Usher's syndrome, Stargardt's disease, Leber's congenital amaurosis, or retinitis pigmentosa. In yet other embodiments, the disease is related to retinopathy, such as diabetic retinopathy, myopic maculopathy. In other embodiments, the disease is an optic neuropathy, such as optic neuritis, non-arteritic anterior ischemic optic neuropathy (NAION), arteritic anterior ischemic optic neuropathy (AION), traumatic optic neuropathy, Leber's optic neuropathy, dominant optic atrophy, recessive optic atrophy, or radiation optic neuropathy.

4.4 Retinal Cells

In some embodiments, the disclosure provides genetically modified retinal cells, comprising a polynucleotide encoding an inhibitor of Dual Leucine Zipper Kinase (DLK), the polynucleotide operatively linked to a promoter. In some embodiments, the inhibitor is capable of binding either (i) an endogenous DLK protein, or (ii) an endogenous mRNA encoding an endogenous DLK. In some embodiments, wherein the inhibitor is capable of reducing the expression, signaling activity, or kinase activity of the endogenous DLK in the retinal cell. Any of the embodiments of features of the polynucleotide described above with respect to vectors can be incorporated in the retinal cells of the disclosure. Indeed it is contemplated that the retinal cells disclosed with have been generated directly or indirectly using the vectors of the disclosure.

In some embodiments, the disclosure provides a method of generating a genetically modified retinal cell, comprising contacting a retinal cell with any vector of the disclosure. The disclosure further provides pharmaceutical compositions comprises any of the vectors or retinal cells of the disclosure.

4.5 Pharmaceutical Compositions and Methods of Treatment

In some embodiments, the disclosure provides a pharmaceutical composition comprising the vector and a pharmaceutically acceptable carrier. In some embodiments, the pharmaceutical composition comprises at least 1e9-1e13 vector genomes (vg) of the vector. In some embodiments, the disclosure provides a unit dose, comprising any of the vectors of the disclosure, wherein the unit does comprises 1e9-1e13 vg of vector in a total volume of 10-200 µL, in some embodiments 50-100 µL.

In some embodiments, the disclosure provides a method of treating a condition in subject in need thereof, comprising administering an effective amount of a pharmaceutical composition of the disclosure to the subject. In some embodiments, the condition is glaucoma, optic neuropathy, retinopathy, retinal detachment, retinitis pigmentosa, retinal dystrophy, macular degeneration, amyotrophic lateral sclerosis (ALS), Parkinson Disease, Alzheimer Disease, prior-related neurodegenerative disease, Huntington's disease, spinocerebellar ataxia, spinal muscular atrophy, multiple system atrophy. In some embodiments, the glaucoma is primary open angle (e.g. chronic glaucoma), normal tension glaucoma, angle closure glaucoma (e.g. acute glaucoma), secondary glaucoma, inherited glaucoma (e.g. pigmentary glaucoma), or myocilin (MYOC) glaucoma. In some embodiments, the neuropathy is Leber hereditary optic neuropathy (LHON) or autosomal dominant optic atrophy (ADOA or DOA). In some embodiments, the retinopathy is retinopathy of prematurity (ROP) or diabetic retinopathy.

In some embodiments, the retinitis pigmentosa is related to Leber congenital amaurosis. The retinitis pigmentosa may be caused by any of the genotypes known to have causative relationship with the condition. Mutations in more than 60 genes are known to cause nonsyndromic retinitis pigmentosa. More than 20 of these genes are associated with the autosomal dominant form of the disorder. Mutations in the RHO gene are the most common cause of autosomal dominant retinitis pigmentosa, accounting for 20 to 30 percent of all cases. At least 35 genes have been associated with the autosomal recessive form of the disorder. The most common of these is USH2A; mutations in this gene are responsible for 10 to 15 percent of all cases of autosomal recessive retinitis pigmentosa. Changes in at least six genes are thought to cause the X-linked form of the disorder. Together, mutations in the RPGR and RP2 genes account for most cases of X-linked retinitis pigmentosa. In some embodiments the retinitis pigmentosa is associated with inheritance of alleles of one or more of genes selected from the group consisting of C2ORF71, C8ORF37, CA4, CERKL, CLRN1, CNGA1, CNGB1, CRB1, CRX, DHDDS, EYS, FAM161A, FSCN2, GUCA1B, IDH3B, IMPDH1, IMPG2, KLHL7, LRAT, MAK, MERTK, NR2E3, NRL, OFD1, PDE6A, PDE6B, PDE6G, PRCD, PROM1, PRPF3, PRPF6, PRPF8, PRPF31, PRPH2, RBP3, RDH12, RGR, RHO, RLBP1, ROM1, RP1, RP2, RP9, RPE65, RPGR, SAG, SEMA4A, SNRNP 200, SPATA7, TOPORS, TTC8, TULP1, USH2A, and ZNF513, as described in Daiger et al. *Clin Genet.* 84:132-141 (2013).

In some embodiments, the retinal dystrophy is Stargardt macular degeneration, rod-cone dystrophy, or cone-rod dystrophy.

EXAMPLES

The invention is further described in the following Examples, which do not limit the scope of the invention described in the claims.

Example 1: Engineering of Improved Dominant-Negative DLK (DN-DLK)

Expression of the leucine zipper domain of DLK has been shown to have a dominant negative effect of DLK function. Nihalani et al. *J. Bio Chem.* 275, 7273-7279 (2000). To attempt to generate improved dominant negative DLKs (DN-DLKs), Applicants identified mutations in the leucine zipper domain intended to (1) increase the affinity of the DLK/DN-DLK heterodimeric interaction and/or (2) decrease the affinity of the DN-DLK/DN-DLK homodimeric interaction, with the aim of favoring disruption of DLK/DLK homodimers in cells.

Using the known pinwheel structure of leucine zippers (FIG. 1A), the sequence DLK (FIG. 1B; SEQ ID NO: 4) was modelled as eight pinwheels (FIG. 2A-2H). Amino-acid substitutions identified by analysis of these models are listed in Table 4.

TABLE 4

Substitutions to Enhance DN-DLKs

| Repeat | Substitutions | Effect |
|---|---|---|
| L1 | Lysine (K) 391 to glutamic acid (E) | Create H-E pair Stabilize heterodimer |
|  | Lysine (K) 391 to aspartic acid (D) | Create H-D pair Stabilize heterodimer |
|  | Histidine (H) 393 to | Create K-E pair |

TABLE 4-continued

Substitutions to Enhance DN-DLKs

| Repeat | Substitutions | Effect |
|---|---|---|
|  | glutamic acid (E) | Stabilize heterodimer |
|  | Histidine (H) 393 to aspartic acid (D) | Create K-D pair Stabilize heterodimer |
| L2 | Lysine (K) 398 to glutamic acid (E) | Create R-E pair Stabilize heterodimer |
|  | Lysine (K) 398 to aspartic acid (D) | Create R-D pair Stabilize heterodimer |
| L3 | Lysine (K) 407 to glutamic acid (E) | Create H-E pair Stabilize heterodimer |
|  | Lysine (K) 407 to aspartic acid (D) | Create H-D pair Stabilize heterodimer |
| L3 | Histidine (H) 405 to glutamic acid (E) | Create L-E pair Destabilize DN-DLK homodimer |
|  | Histidine (H) 405 to aspartic acid (D) | Create L-D pair Destabilize DN-DLK homodimer |
| L4 | Valine (V) 412 to glutamic acid (E) | Create E-R pair Stabilize heterodimer |
|  | Valine (V) 412 to aspartic acid | Create D-R pair Stabilize heterodimer |
| L4 | Arginine (R) 414 to glutamic acid (E) | Create E-R pair Destabilize DN-DLK homodimer |
|  | Arginine (R) 414 to aspartic acid (D) | Create D-R pair Destabilize DN-DLK homodimer |
| L5 | N/A | N/A |
| L6 | Lysine (K) 407 to glutamic acid (E) | Create R-E pair |
|  | Lysine (K) 407 to aspartic acid (D) | Create R-D pair |
| L7 | Leucine (L) 458 to glutamic acid (E) | Create L-E pair, Destabilize DN-DLK homodimer |
|  | Leucine (L) 458 to aspartic acid (D) | Create L-D pair Destabilize DN-DLK homodimer |
| L7 | Glutamic acid (E) 454 to A, V, I, L, M, F, W | Strengthen hydrophobic core |
|  | Glutamic acid (E) 454 to R, H, K | Create electrostatic interaction. |
| L8 | Glutamic acid (E) 461 to A, V, I, L, M, F, W | Strengthen hydrophobic core |
|  | Glutamic acid (E) 461 to R, H, K | Create electrostatic interaction. |

Polynucleotides encoding DLK fragments with various combinations of the substitutions listed in Table 5 are generated. Polynucleotides encoding DLK fragments with combinations of two or more of the substitutions listed in Table 5 are generated. A polynucleotide encoding a DLK fragment with ten substitutions is generated (SEQ ID NO: 6). A polynucleotide encoding a larger DLK fragment with the same ten substitutions is generated (SEQ ID NO: 7). These designs are tested by expression as isolated DLK fragments and as mutations in full-length DLK.

TABLE 5

Exemplary Dominant-Negative Dual-Leucine Zipper Kinase Sequences

| Sequence description | Sequence | SEQ ID NO |
|---|---|---|
| Modified DLK Zipper 1, bridge, and zipper 2. Modifications in bold enhance heterodimerization with DLK, compared to DLK homodimers or LZ-LZ homodimers | REEVELEFEKIRSEGTCLEREEEELEMERREELRHALDIRE HYERKLERANNLYMELNALMLQLELRERELEREEQALER R | 6 |
| Longer LZ domain with same modifications | LSTPQETYFKSQAEWREEVELEFEKIRSEGTCLEREEEEL EMERREELRHALDIREHYERKLERANNLYMELNALMLQL ELRERELEREEQALERRCPGLLKPHPSRGLLHGNTME | 7 |
| Kinase domain of kinase-dead DLK (K152A) | ILDLQWVGSGAQGAVFLGRFHGEEVAVAAKVRDLKETDI KHLRKLKHPNIITFKGVCTQAPCYCILMEFCAQGQLYEV LRAGRPVTPSLLVDWSMGIAGGMNYLHLHKIIHRDLKSP NMLITYDDVVKISDFGTSKELSDKSTKMSFAGTVAWMA PEVIRNEPVSEKVDIWSFGVVLWELLTGEIPYKDVDSSAII WGVGSNSLHLPVPSSCPDGFKILLRQCWNSKPRNRPSFR QILLHLDI | 8 |

Alternatively or in conjunction with any of these mutations to the leucine zipper domain, the kinase domain of DLK may be either deleted or replaced with a kinase-dead kinase domain. One exemplary kinase-dead kinase domain is a kinase domain with the K152A substitution, which replaces lysine K152 with alanine (A), as shown in SEQ ID NO: 8.

The various constructs are tested for in vitro competition with native DLK and for in vivo inhibition of DLK kinase activity or downstream signaling.

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

What is claimed:

1. An inhibitor, comprising a protein comprising a leucine zipper domain that shares at least 95% identity to SEQ ID NO: 1, wherein the leucine zipper domain comprises at least one substitution at one or more of the positions 391 and 393.

2. The inhibitor of claim 1, wherein said substitutions comprise at least one of:
   a) K391 to D or K391 to E, and/or
   b) H393 to D or H393 to E.

3. The inhibitor of claim 1, wherein the leucine zipper domain further comprises one or more additional substitutions at one or more positions, related to SEQ ID NO: 1 selected from one or more of (a) through (h):
   a) K398,
   b) L407,
   c) H405,
   d) V412,
   e) R414,
   f) K453,
   g) L458, and
   h) R460.

4. The inhibitor of claim 1, wherein the substitutions either (i) increase affinity of the leucine zipper domain for endogenous dual leucine zipper kinase (DLK), or (ii) decrease affinity of the leucine zipper domain for itself; each of (i) and (ii) as compared to the same leucine zipper domain having the native residue at the position of the substitution.

5. The inhibitor of claim 4, wherein the leucine zipper domain preferentially forms heterodimers with endogenous DLK compared to either one of (i) homodimers of the leucine zipper domain or (ii) DLK homodimers.

6. The inhibitor of claim 1, wherein the inhibitor further comprises DLK kinase domain having at least 95% identity to SEQ ID NO: 5, wherein the DLK kinase domain comprises a substitution that decreases the kinase activity of the DLK kinase domain.

7. The inhibitor of claim 6, wherein the DLK kinase domain comprises SEQ ID NO: 8.

8. The inhibitor of claim 1, wherein the inhibitor further comprises a functional fragment of mixed lineage kinase (LZK).

9. The inhibitor of claim 1, wherein the inhibitor further comprises a neurotrophic factor brain-derived neurotrophic factor (BDNF), glial cell-derived neurotrophic factor (GDNF), neurotrophin-4 (NT4), tropomyosin receptor kinase B (TrkB), or rod-derived cone viability factor (RdCVF), ciliary neurotrophic factor (CNTF).

10. A recombinant viral vector, comprising an expression cassette comprising a polynucleotide encoding the inhibitor of claim 1 operably linked to a promoter.

11. The vector of claim 10, wherein the vector is a recombinant adeno-associated virus (rAAV) vector.

12. The vector of claim 10, wherein the vector comprises a capsid of serotype AAV1, AAV2, AAV4, AAV5, AAV7, AAV8, AAV9, AAV2/2 (7m8), or Anc80L65.

13. The vector of claim 10, wherein the ubiquitous promoter comprises a CMV promoter, a CAG promoter, CBA promoter, or a CBh promoter.

14. The vector of claim 10, wherein the promoter is a rod photoreceptor-specific promoter.

15. A genetically modified retinal cell, comprising a polynucleotide encoding the leucine zipper domain of claim 1, the polynucleotide operatively linked to a promoter,
wherein the leucine zipper domain is capable of binding either (i) an endogenous DLK protein, or (ii) an endogenous mRNA encoding an endogenous DLK; and
wherein the leucine zipper domain is capable of reducing the expression, signaling activity, or kinase activity of the endogenous DLK in the retinal cell.

16. An inhibitor, comprising a protein comprising a leucine zipper domain that shares at least 95% identity to SEQ ID NO: 1, having at least one substitution, wherein said at least one substitution, individually or collectively, either (i) increases the binding affinity of the leucine zipper domain for endogenous dual leucine zipper kinase (DLK) or (ii) decreases affinity of said inhibitor for itself, compared to the corresponding protein without said at least one substitution.

* * * * *

```
                        SEQUENCE LISTING

<160> NUMBER OF SEQ ID NOS: 26

<210> SEQ ID NO 1
<211> LENGTH: 859
<212> TYPE: PRT
<213> ORGANISM: Homo sapiens

<400> SEQUENCE: 1

Met Ala Cys Leu His Glu Thr Arg Thr Pro Ser Pro Ser Phe Gly Gly
1               5                   10                  15

Phe Val Ser Thr Leu Ser Glu Ala Ser Met Arg Lys Leu Asp Pro Asp
            20                  25                  30

Thr Ser Asp Cys Thr Pro Glu Lys Asp Leu Thr Pro Thr His Val Leu
        35                  40                  45

Gln Leu His Glu Gln Asp Ala Gly Pro Gly Gly Ala Ala Gly Ser
    50                  55                  60

Pro Glu Ser Arg Ala Ser Arg Val Arg Ala Asp Glu Val Arg Leu Gln
65                  70                  75                  80

Cys Gln Ser Gly Ser Gly Phe Leu Glu Gly Leu Phe Gly Cys Leu Arg
                85                  90                  95

Pro Val Trp Thr Met Ile Gly Lys Ala Tyr Ser Thr Glu His Lys Gln
            100                 105                 110

Gln Gln Glu Asp Leu Trp Glu Val Pro Phe Glu Glu Ile Leu Asp Leu
        115                 120                 125

Gln Trp Val Gly Ser Gly Ala Gln Gly Ala Val Phe Leu Gly Arg Phe
    130                 135                 140

His Gly Glu Glu Val Ala Val Lys Lys Val Arg Asp Leu Lys Glu Thr
145                 150                 155                 160

Asp Ile Lys His Leu Arg Lys Leu Lys His Pro Asn Ile Ile Thr Phe
                165                 170                 175

Lys Gly Val Cys Thr Gln Ala Pro Cys Tyr Cys Ile Leu Met Glu Phe
            180                 185                 190

Cys Ala Gln Gly Gln Leu Tyr Glu Val Leu Arg Ala Gly Arg Pro Val
        195                 200                 205

Thr Pro Ser Leu Leu Val Asp Trp Ser Met Gly Ile Ala Gly Gly Met
    210                 215                 220

Asn Tyr Leu His Leu His Lys Ile Ile His Arg Asp Leu Lys Ser Pro
225                 230                 235                 240

Asn Met Leu Ile Thr Tyr Asp Asp Val Val Lys Ile Ser Asp Phe Gly
                245                 250                 255

Thr Ser Lys Glu Leu Ser Asp Lys Ser Thr Lys Met Ser Phe Ala Gly
            260                 265                 270

Thr Val Ala Trp Met Ala Pro Glu Val Ile Arg Asn Glu Pro Val Ser
        275                 280                 285
```

```
Glu Lys Val Asp Ile Trp Ser Phe Gly Val Leu Trp Glu Leu Leu
    290                 295                 300

Thr Gly Glu Ile Pro Tyr Lys Asp Val Asp Ser Ser Ala Ile Ile Trp
305                 310                 315                 320

Gly Val Gly Ser Asn Ser Leu His Leu Pro Val Pro Ser Ser Cys Pro
                325                 330                 335

Asp Gly Phe Lys Ile Leu Leu Arg Gln Cys Trp Asn Ser Lys Pro Arg
            340                 345                 350

Asn Arg Pro Ser Phe Arg Gln Ile Leu Leu His Leu Asp Ile Ala Ser
        355                 360                 365

Ala Asp Val Leu Ser Thr Pro Gln Glu Thr Tyr Phe Lys Ser Gln Ala
370                 375                 380

Glu Trp Arg Glu Glu Val Lys Leu His Phe Glu Lys Ile Lys Ser Glu
385                 390                 395                 400

Gly Thr Cys Leu His Arg Leu Glu Glu Glu Leu Val Met Arg Arg Arg
                405                 410                 415

Glu Glu Leu Arg His Ala Leu Asp Ile Arg Glu His Tyr Glu Arg Lys
            420                 425                 430

Leu Glu Arg Ala Asn Asn Leu Tyr Met Glu Leu Asn Ala Leu Met Leu
        435                 440                 445

Gln Leu Glu Leu Lys Glu Arg Glu Leu Leu Arg Arg Glu Gln Ala Leu
    450                 455                 460

Glu Arg Arg Cys Pro Gly Leu Leu Lys Pro His Pro Ser Arg Gly Leu
465                 470                 475                 480

Leu His Gly Asn Thr Met Glu Lys Leu Ile Lys Lys Arg Asn Val Pro
                485                 490                 495

Gln Lys Leu Ser Pro His Ser Lys Arg Pro Asp Ile Leu Lys Thr Glu
            500                 505                 510

Ser Leu Leu Pro Lys Leu Asp Ala Ala Leu Ser Gly Val Gly Leu Pro
        515                 520                 525

Gly Cys Pro Lys Gly Pro Pro Ser Pro Gly Arg Ser Arg Arg Gly Lys
    530                 535                 540

Thr Arg His Arg Lys Ala Ser Ala Lys Gly Ser Cys Gly Asp Leu Pro
545                 550                 555                 560

Gly Leu Arg Thr Ala Val Pro Pro His Glu Pro Gly Gly Pro Gly Ser
                565                 570                 575

Pro Gly Gly Leu Gly Gly Gly Pro Ser Ala Trp Glu Ala Cys Pro Pro
            580                 585                 590

Ala Leu Arg Gly Leu His His Asp Leu Leu Arg Lys Met Ser Ser
        595                 600                 605

Ser Ser Pro Asp Leu Leu Ser Ala Ala Leu Gly Ser Arg Gly Arg Gly
    610                 615                 620

Ala Thr Gly Gly Ala Gly Asp Pro Gly Ser Pro Pro Ala Arg Gly
625                 630                 635                 640

Asp Thr Pro Pro Ser Glu Gly Ser Ala Pro Gly Ser Thr Ser Pro Asp
                645                 650                 655

Ser Pro Gly Gly Ala Lys Gly Glu Pro Pro Pro Val Gly Pro Gly
            660                 665                 670

Glu Gly Val Gly Leu Leu Gly Thr Gly Arg Glu Gly Thr Ser Gly Arg
        675                 680                 685

Gly Gly Ser Arg Ala Gly Ser Gln His Leu Thr Pro Ala Ala Leu Leu
    690                 695                 700
```

-continued

Tyr Arg Ala Ala Val Thr Arg Ser Gln Lys Arg Gly Ile Ser Ser Glu
705                 710                 715                 720

Glu Glu Glu Gly Glu Val Asp Ser Glu Val Glu Leu Thr Ser Ser Gln
            725                 730                 735

Arg Trp Pro Gln Ser Leu Asn Met Arg Gln Ser Leu Ser Thr Phe Ser
                740                 745                 750

Ser Glu Asn Pro Ser Asp Gly Glu Gly Thr Ala Ser Glu Pro Ser
            755                 760                 765

Pro Ser Gly Thr Pro Glu Val Gly Ser Thr Asn Thr Asp Glu Arg Pro
            770                 775                 780

Asp Glu Arg Ser Asp Asp Met Cys Ser Gln Gly Ser Glu Ile Pro Leu
785                 790                 795                 800

Asp Pro Pro Pro Ser Glu Val Ile Pro Gly Pro Glu Pro Ser Ser Leu
                805                 810                 815

Pro Ile Pro His Gln Glu Leu Leu Arg Glu Arg Gly Pro Pro Asn Ser
                820                 825                 830

Glu Asp Ser Asp Cys Asp Ser Thr Glu Leu Asp Asn Ser Asn Ser Val
            835                 840                 845

Asp Ala Leu Arg Pro Pro Ala Ser Leu Pro Pro
    850                 855

<210> SEQ ID NO 2
<211> LENGTH: 892
<212> TYPE: PRT
<213> ORGANISM: Homo sapiens

<400> SEQUENCE: 2

Met Ala Cys Leu His Glu Thr Arg Thr Pro Ser Pro Ser Phe Gly Gly
1               5                   10                  15

Phe Val Ser Thr Leu Ser Glu Ala Ser Met Arg Lys Leu Asp Pro Asp
                20                  25                  30

Thr Ser Asp Cys Thr Pro Glu Lys Asp Leu Thr Pro Thr Gln Cys Val
            35                  40                  45

Leu Arg Asp Val Val Pro Leu Gly Gly Gln Gly Gly Gly Pro Ser
50                  55                  60

Pro Ser Pro Gly Gly Glu Pro Pro Glu Pro Phe Ala Asn Ser Val
65                  70                  75                  80

Leu Gln Leu His Glu Gln Asp Ala Gly Pro Gly Gly Ala Ala Gly
                85                  90                  95

Ser Pro Glu Ser Arg Ala Ser Arg Val Arg Ala Asp Glu Val Arg Leu
            100                 105                 110

Gln Cys Gln Ser Gly Ser Gly Phe Leu Glu Gly Leu Phe Gly Cys Leu
        115                 120                 125

Arg Pro Val Trp Thr Met Ile Gly Lys Ala Tyr Ser Thr Glu His Lys
    130                 135                 140

Gln Gln Gln Glu Asp Leu Trp Glu Val Pro Phe Glu Glu Ile Leu Asp
145                 150                 155                 160

Leu Gln Trp Val Gly Ser Gly Ala Gln Gly Ala Val Phe Leu Gly Arg
                165                 170                 175

Phe His Gly Glu Glu Val Ala Val Lys Lys Val Arg Asp Leu Lys Glu
                180                 185                 190

Thr Asp Ile Lys His Leu Arg Lys Leu Lys His Pro Asn Ile Ile Thr
            195                 200                 205

Phe Lys Gly Val Cys Thr Gln Ala Pro Cys Tyr Cys Ile Leu Met Glu
    210                 215                 220

```
Phe Cys Ala Gln Gly Gln Leu Tyr Glu Val Leu Arg Ala Gly Arg Pro
225                 230                 235                 240

Val Thr Pro Ser Leu Leu Val Asp Trp Ser Met Gly Ile Ala Gly Gly
            245                 250                 255

Met Asn Tyr Leu His Leu His Lys Ile Ile His Arg Asp Leu Lys Ser
        260                 265                 270

Pro Asn Met Leu Ile Thr Tyr Asp Asp Val Val Lys Ile Ser Asp Phe
    275                 280                 285

Gly Thr Ser Lys Glu Leu Ser Asp Lys Ser Thr Lys Met Ser Phe Ala
290                 295                 300

Gly Thr Val Ala Trp Met Ala Pro Glu Val Ile Arg Asn Glu Pro Val
305                 310                 315                 320

Ser Glu Lys Val Asp Ile Trp Ser Phe Gly Val Val Leu Trp Glu Leu
            325                 330                 335

Leu Thr Gly Glu Ile Pro Tyr Lys Asp Val Asp Ser Ser Ala Ile Ile
        340                 345                 350

Trp Gly Val Gly Ser Asn Ser Leu His Leu Pro Val Pro Ser Ser Cys
    355                 360                 365

Pro Asp Gly Phe Lys Ile Leu Leu Arg Gln Cys Trp Asn Ser Lys Pro
370                 375                 380

Arg Asn Arg Pro Ser Phe Arg Gln Ile Leu Leu His Leu Asp Ile Ala
385                 390                 395                 400

Ser Ala Asp Val Leu Ser Thr Pro Gln Glu Thr Tyr Phe Lys Ser Gln
            405                 410                 415

Ala Glu Trp Arg Glu Glu Val Lys Leu His Phe Glu Lys Ile Lys Ser
        420                 425                 430

Glu Gly Thr Cys Leu His Arg Leu Glu Glu Leu Val Met Arg Arg
    435                 440                 445

Arg Glu Glu Leu Arg His Ala Leu Asp Ile Arg Glu His Tyr Glu Arg
450                 455                 460

Lys Leu Glu Arg Ala Asn Asn Leu Tyr Met Glu Leu Asn Ala Leu Met
465                 470                 475                 480

Leu Gln Leu Glu Leu Lys Glu Arg Glu Leu Leu Arg Arg Glu Gln Ala
            485                 490                 495

Leu Glu Arg Arg Cys Pro Gly Leu Leu Lys Pro His Pro Ser Arg Gly
        500                 505                 510

Leu Leu His Gly Asn Thr Met Glu Lys Leu Ile Lys Lys Arg Asn Val
    515                 520                 525

Pro Gln Lys Leu Ser Pro His Ser Lys Arg Pro Asp Ile Leu Lys Thr
530                 535                 540

Glu Ser Leu Leu Pro Lys Leu Asp Ala Ala Leu Ser Gly Val Gly Leu
545                 550                 555                 560

Pro Gly Cys Pro Lys Gly Pro Pro Ser Pro Gly Arg Ser Arg Arg Gly
            565                 570                 575

Lys Thr Arg His Arg Lys Ala Ser Ala Lys Gly Ser Cys Gly Asp Leu
        580                 585                 590

Pro Gly Leu Arg Thr Ala Val Pro Pro His Glu Pro Gly Pro Gly
    595                 600                 605

Ser Pro Gly Gly Leu Gly Gly Pro Ser Ala Trp Glu Ala Cys Pro
610                 615                 620

Pro Ala Leu Arg Gly Leu His His Asp Leu Leu Leu Arg Lys Met Ser
625                 630                 635                 640
```

```
Ser Ser Ser Pro Asp Leu Leu Ser Ala Ala Leu Gly Ser Arg Gly Arg
                645                 650                 655

Gly Ala Thr Gly Gly Ala Gly Asp Pro Gly Ser Pro Pro Ala Arg
        660                 665                 670

Gly Asp Thr Pro Pro Ser Glu Gly Ser Ala Pro Gly Ser Thr Ser Pro
        675                 680                 685

Asp Ser Pro Gly Gly Ala Lys Gly Glu Pro Pro Pro Val Gly Pro
    690                 695                 700

Gly Glu Gly Val Gly Leu Gly Thr Gly Arg Gly Thr Ser Gly
705                 710                 715                 720

Arg Gly Gly Ser Arg Ala Gly Ser Gln His Leu Thr Pro Ala Ala Leu
                725                 730                 735

Leu Tyr Arg Ala Ala Val Thr Arg Ser Gln Lys Arg Gly Ile Ser Ser
            740                 745                 750

Glu Glu Glu Glu Gly Glu Val Asp Ser Glu Val Glu Leu Thr Ser Ser
        755                 760                 765

Gln Arg Trp Pro Gln Ser Leu Asn Met Arg Gln Ser Leu Ser Thr Phe
    770                 775                 780

Ser Ser Glu Asn Pro Ser Asp Gly Glu Glu Gly Thr Ala Ser Glu Pro
785                 790                 795                 800

Ser Pro Ser Gly Thr Pro Glu Val Gly Ser Thr Asn Thr Asp Glu Arg
                805                 810                 815

Pro Asp Glu Arg Ser Asp Asp Met Cys Ser Gln Gly Ser Glu Ile Pro
            820                 825                 830

Leu Asp Pro Pro Ser Glu Val Ile Pro Gly Pro Glu Pro Ser Ser
        835                 840                 845

Leu Pro Ile Pro His Gln Glu Leu Leu Arg Glu Arg Gly Pro Pro Asn
    850                 855                 860

Ser Glu Asp Ser Asp Cys Asp Ser Thr Glu Leu Asp Asn Ser Asn Ser
865                 870                 875                 880

Val Asp Ala Leu Arg Pro Pro Ala Ser Leu Pro Pro
                885                 890

<210> SEQ ID NO 3
<211> LENGTH: 116
<212> TYPE: PRT
<213> ORGANISM: Homo sapiens

<400> SEQUENCE: 3

Leu Ser Thr Pro Gln Glu Thr Tyr Phe Lys Ser Gln Ala Glu Trp Arg
1               5                   10                  15

Glu Glu Val Lys Leu His Phe Glu Lys Ile Lys Ser Glu Gly Thr Cys
            20                  25                  30

Leu His Arg Leu Glu Glu Glu Leu Val Met Arg Arg Glu Glu Leu
        35                  40                  45

Arg His Ala Leu Asp Ile Arg Glu His Tyr Glu Arg Lys Leu Glu Arg
    50                  55                  60

Ala Asn Asn Leu Tyr Met Glu Leu Asn Ala Leu Met Leu Gln Leu Glu
65                  70                  75                  80

Leu Lys Glu Arg Glu Leu Leu Arg Arg Glu Gln Ala Leu Glu Arg Arg
                85                  90                  95

Cys Pro Gly Leu Leu Lys Pro His Pro Ser Arg Gly Leu Leu His Gly
            100                 105                 110

Asn Thr Met Glu
        115
```

<210> SEQ ID NO 4
<211> LENGTH: 81
<212> TYPE: PRT
<213> ORGANISM: Homo sapiens

<400> SEQUENCE: 4

```
Arg Glu Glu Val Lys Leu His Phe Glu Lys Ile Lys Ser Glu Gly Thr
1               5                   10                  15
Cys Leu His Arg Leu Glu Glu Leu Val Met Arg Arg Glu Glu
                20                  25                  30
Leu Arg His Ala Leu Asp Ile Arg Glu His Tyr Glu Arg Lys Leu Glu
            35                  40                  45
Arg Ala Asn Asn Leu Tyr Met Glu Leu Asn Ala Leu Met Leu Gln Leu
        50                  55                  60
Glu Leu Lys Glu Arg Glu Leu Arg Arg Glu Gln Ala Leu Glu Arg
65                  70                  75                  80
Arg
```

<210> SEQ ID NO 5
<211> LENGTH: 242
<212> TYPE: PRT
<213> ORGANISM: Homo sapiens

<400> SEQUENCE: 5

```
Ile Leu Asp Leu Gln Trp Val Gly Ser Gly Ala Gln Gly Ala Val Phe
1               5                   10                  15
Leu Gly Arg Phe His Gly Glu Glu Val Ala Val Lys Lys Val Arg Asp
                20                  25                  30
Leu Lys Glu Thr Asp Ile Lys His Leu Arg Lys Leu Lys His Pro Asn
            35                  40                  45
Ile Ile Thr Phe Lys Gly Val Cys Thr Gln Ala Pro Cys Tyr Cys Ile
        50                  55                  60
Leu Met Glu Phe Cys Ala Gln Gly Gln Leu Tyr Glu Val Leu Arg Ala
65                  70                  75                  80
Gly Arg Pro Val Thr Pro Ser Leu Leu Val Asp Trp Ser Met Gly Ile
                85                  90                  95
Ala Gly Gly Met Asn Tyr Leu His Leu His Lys Ile Ile His Arg Asp
                100                 105                 110
Leu Lys Ser Pro Asn Met Leu Ile Thr Tyr Asp Asp Val Val Lys Ile
            115                 120                 125
Ser Asp Phe Gly Thr Ser Lys Glu Leu Ser Asp Lys Ser Thr Lys Met
        130                 135                 140
Ser Phe Ala Gly Thr Val Ala Trp Met Ala Pro Glu Val Ile Arg Asn
145                 150                 155                 160
Glu Pro Val Ser Glu Lys Val Asp Ile Trp Ser Phe Gly Val Val Leu
                165                 170                 175
Trp Glu Leu Leu Thr Gly Glu Ile Pro Tyr Lys Asp Val Asp Ser Ser
                180                 185                 190
Ala Ile Ile Trp Gly Val Gly Ser Asn Ser Leu His Leu Pro Val Pro
            195                 200                 205
Ser Ser Cys Pro Asp Gly Phe Lys Ile Leu Leu Arg Gln Cys Trp Asn
        210                 215                 220
Ser Lys Pro Arg Asn Arg Pro Ser Phe Arg Gln Ile Leu Leu His Leu
225                 230                 235                 240
```

Asp Ile

<210> SEQ ID NO 6
<211> LENGTH: 81
<212> TYPE: PRT
<213> ORGANISM: Artificial Sequence
<220> FEATURE:
<223> OTHER INFORMATION: Made in Lab protein sequence

<400> SEQUENCE: 6

Arg Glu Glu Val Glu Leu Glu Phe Glu Lys Ile Arg Ser Glu Gly Thr
1               5                   10                  15

Cys Leu Glu Arg Glu Glu Glu Leu Glu Met Glu Arg Arg Glu Glu
            20                  25                  30

Leu Arg His Ala Leu Asp Ile Arg Glu His Tyr Glu Arg Lys Leu Glu
        35                  40                  45

Arg Ala Asn Asn Leu Tyr Met Glu Leu Asn Ala Leu Met Leu Gln Leu
    50                  55                  60

Glu Leu Arg Glu Arg Glu Leu Glu Arg Glu Gln Ala Leu Glu Arg
65                  70                  75                  80

Arg

<210> SEQ ID NO 7
<211> LENGTH: 116
<212> TYPE: PRT
<213> ORGANISM: Artificial Sequence
<220> FEATURE:
<223> OTHER INFORMATION: Made in Lab protein sequence

<400> SEQUENCE: 7

Leu Ser Thr Pro Gln Glu Thr Tyr Phe Lys Ser Gln Ala Glu Trp Arg
1               5                   10                  15

Glu Glu Val Glu Leu Glu Phe Glu Lys Ile Arg Ser Glu Gly Thr Cys
            20                  25                  30

Leu Glu Arg Glu Glu Glu Leu Glu Met Glu Arg Arg Glu Glu Leu
        35                  40                  45

Arg His Ala Leu Asp Ile Arg Glu His Tyr Glu Arg Lys Leu Glu Arg
    50                  55                  60

Ala Asn Asn Leu Tyr Met Glu Leu Asn Ala Leu Met Leu Gln Leu Glu
65                  70                  75                  80

Leu Arg Glu Arg Glu Leu Arg Glu Gln Ala Leu Glu Arg Arg
            85                  90                  95

Cys Pro Gly Leu Leu Lys Pro His Pro Ser Arg Gly Leu Leu His Gly
            100                 105                 110

Asn Thr Met Glu
    115

<210> SEQ ID NO 8
<211> LENGTH: 242
<212> TYPE: PRT
<213> ORGANISM: Artificial Sequence
<220> FEATURE:
<223> OTHER INFORMATION: Made in Lab protein sequence

<400> SEQUENCE: 8

Ile Leu Asp Leu Gln Trp Val Gly Ser Gly Ala Gln Gly Ala Val Phe
1               5                   10                  15

Leu Gly Arg Phe His Gly Glu Glu Val Ala Val Ala Lys Val Arg Asp
            20                  25                  30

Leu Lys Glu Thr Asp Ile Lys His Leu Arg Lys Leu Lys His Pro Asn
            35                  40                  45

Ile Ile Thr Phe Lys Gly Val Cys Thr Gln Ala Pro Cys Tyr Cys Ile
 50                  55                  60

Leu Met Glu Phe Cys Ala Gln Gly Gln Leu Tyr Glu Val Leu Arg Ala
 65                  70                  75                  80

Gly Arg Pro Val Thr Pro Ser Leu Leu Val Asp Trp Ser Met Gly Ile
                 85                  90                  95

Ala Gly Gly Met Asn Tyr Leu His Leu His Lys Ile Ile His Arg Asp
             100                 105                 110

Leu Lys Ser Pro Asn Met Leu Ile Thr Tyr Asp Asp Val Val Lys Ile
         115                 120                 125

Ser Asp Phe Gly Thr Ser Lys Glu Leu Ser Asp Lys Ser Thr Lys Met
130                 135                 140

Ser Phe Ala Gly Thr Val Ala Trp Met Ala Pro Glu Val Ile Arg Asn
145                 150                 155                 160

Glu Pro Val Ser Glu Lys Val Asp Ile Trp Ser Phe Gly Val Val Leu
                165                 170                 175

Trp Glu Leu Leu Thr Gly Glu Ile Pro Tyr Lys Asp Val Asp Ser Ser
                180                 185                 190

Ala Ile Ile Trp Gly Val Gly Ser Asn Ser Leu His Leu Pro Val Pro
            195                 200                 205

Ser Ser Cys Pro Asp Gly Phe Lys Ile Leu Leu Arg Gln Cys Trp Asn
        210                 215                 220

Ser Lys Pro Arg Asn Arg Pro Ser Phe Arg Gln Ile Leu Leu His Leu
225                 230                 235                 240

Asp Ile

<210> SEQ ID NO 9
<211> LENGTH: 28
<212> TYPE: PRT
<213> ORGANISM: Artificial Sequence
<220> FEATURE:
<223> OTHER INFORMATION: Made in Lab protein sequence
<220> FEATURE:
<221> NAME/KEY: MOD_RES
<222> LOCATION: (5)..(5)
<223> OTHER INFORMATION: Xaa = Glu or Asp
<220> FEATURE:
<221> NAME/KEY: MOD_RES
<222> LOCATION: (7)..(7)
<223> OTHER INFORMATION: Xaa = Glu or Asp
<220> FEATURE:
<221> NAME/KEY: MOD_RES
<222> LOCATION: (12)..(12)
<223> OTHER INFORMATION: Xaa = Arg, His or Lys
<220> FEATURE:
<221> NAME/KEY: MOD_RES
<222> LOCATION: (19)..(19)
<223> OTHER INFORMATION: Xaa = Glu or Asp
<220> FEATURE:
<221> NAME/KEY: MOD_RES
<222> LOCATION: (21)..(21)
<223> OTHER INFORMATION: Xaa = Glu or Asp
<220> FEATURE:
<221> NAME/KEY: MOD_RES
<222> LOCATION: (26)..(26)
<223> OTHER INFORMATION: Xaa = Glu or Asp
<220> FEATURE:
<221> NAME/KEY: MOD_RES
<222> LOCATION: (28)..(28)
<223> OTHER INFORMATION: Xaa = Glu or Asp

<400> SEQUENCE: 9

```
Arg Glu Glu Val Xaa Leu Xaa Phe Glu Lys Ile Xaa Ser Glu Gly Thr
1               5                   10                  15

Cys Leu Xaa Arg Xaa Glu Glu Glu Leu Xaa Met Xaa
            20                  25
```

<210> SEQ ID NO 10
<211> LENGTH: 28
<212> TYPE: PRT
<213> ORGANISM: Artificial Sequence
<220> FEATURE:
<223> OTHER INFORMATION: Made in Lab protein sequence
<220> FEATURE:
<221> NAME/KEY: MOD_RES
<222> LOCATION: (14)..(14)
<223> OTHER INFORMATION: Xaa = Arg, His or Lys
<220> FEATURE:
<221> NAME/KEY: MOD_RES
<222> LOCATION: (19)..(19)
<223> OTHER INFORMATION: Xaa = Glu or Asp
<220> FEATURE:
<221> NAME/KEY: MOD_RES
<222> LOCATION: (21)..(21)
<223> OTHER INFORMATION: Xaa = Glu or Asp

<400> SEQUENCE: 10

```
Tyr Met Glu Leu Asn Ala Leu Met Leu Gln Leu Glu Leu Xaa Glu Arg
1               5                   10                  15

Glu Leu Xaa Arg Xaa Glu Gln Ala Leu Glu Arg Arg
            20                  25
```

<210> SEQ ID NO 11
<211> LENGTH: 25
<212> TYPE: PRT
<213> ORGANISM: Homo sapiens

<400> SEQUENCE: 11

```
Arg Arg Glu Glu Leu Arg His Ala Leu Asp Ile Arg Glu His Tyr Glu
1               5                   10                  15

Arg Lys Leu Glu Arg Ala Asn Asn Leu
            20                  25
```

<210> SEQ ID NO 12
<211> LENGTH: 28
<212> TYPE: PRT
<213> ORGANISM: Artificial Sequence
<220> FEATURE:
<223> OTHER INFORMATION: Made in Lab protein sequence
<220> FEATURE:
<221> NAME/KEY: MOD_RES
<222> LOCATION: (12)..(12)
<223> OTHER INFORMATION: Xaa = Arg, His or Lys
<220> FEATURE:
<221> NAME/KEY: MOD_RES
<222> LOCATION: (19)..(19)
<223> OTHER INFORMATION: Xaa = Glu or Asp
<220> FEATURE:
<221> NAME/KEY: MOD_RES
<222> LOCATION: (21)..(21)
<223> OTHER INFORMATION: Xaa = Glu or Asp
<220> FEATURE:
<221> NAME/KEY: MOD_RES
<222> LOCATION: (26)..(26)
<223> OTHER INFORMATION: Xaa = Glu or Asp
<220> FEATURE:
<221> NAME/KEY: MOD_RES
<222> LOCATION: (28)..(28)
<223> OTHER INFORMATION: Xaa = Glu or Asp

<400> SEQUENCE: 12

```
Arg Glu Glu Val Asp Leu Asp Phe Glu Lys Ile Xaa Ser Glu Gly Thr
```

```
1               5                   10                  15
Cys Leu Xaa Arg Xaa Glu Glu Glu Leu Xaa Met Xaa
            20                  25

<210> SEQ ID NO 13
<211> LENGTH: 28
<212> TYPE: PRT
<213> ORGANISM: Artificial Sequence
<220> FEATURE:
<223> OTHER INFORMATION: Made in Lab protein sequence
<220> FEATURE:
<221> NAME/KEY: MOD_RES
<222> LOCATION: (12)..(12)
<223> OTHER INFORMATION: Xaa = Arg, His or Lys
<220> FEATURE:
<221> NAME/KEY: MOD_RES
<222> LOCATION: (19)..(19)
<223> OTHER INFORMATION: Xaa = Glu or Asp
<220> FEATURE:
<221> NAME/KEY: MOD_RES
<222> LOCATION: (21)..(21)
<223> OTHER INFORMATION: Xaa = Glu or Asp
<220> FEATURE:
<221> NAME/KEY: MOD_RES
<222> LOCATION: (26)..(26)
<223> OTHER INFORMATION: Xaa = Glu or Asp
<220> FEATURE:
<221> NAME/KEY: MOD_RES
<222> LOCATION: (28)..(28)
<223> OTHER INFORMATION: Xaa = Glu or Asp

<400> SEQUENCE: 13

Arg Glu Glu Val Glu Leu Asp Phe Glu Lys Ile Xaa Ser Glu Gly Thr
1               5                   10                  15

Cys Leu Xaa Arg Xaa Glu Glu Glu Leu Xaa Met Xaa
            20                  25

<210> SEQ ID NO 14
<211> LENGTH: 28
<212> TYPE: PRT
<213> ORGANISM: Artificial Sequence
<220> FEATURE:
<223> OTHER INFORMATION: Made in Lab protein sequence
<220> FEATURE:
<221> NAME/KEY: MOD_RES
<222> LOCATION: (12)..(12)
<223> OTHER INFORMATION: Xaa = Arg, His or Lys
<220> FEATURE:
<221> NAME/KEY: MOD_RES
<222> LOCATION: (19)..(19)
<223> OTHER INFORMATION: Xaa = Glu or Asp
<220> FEATURE:
<221> NAME/KEY: MOD_RES
<222> LOCATION: (21)..(21)
<223> OTHER INFORMATION: Xaa = Glu or Asp
<220> FEATURE:
<221> NAME/KEY: MOD_RES
<222> LOCATION: (26)..(26)
<223> OTHER INFORMATION: Xaa = Glu or Asp
<220> FEATURE:
<221> NAME/KEY: MOD_RES
<222> LOCATION: (28)..(28)
<223> OTHER INFORMATION: Xaa = Glu or Asp

<400> SEQUENCE: 14

Arg Glu Glu Val Asp Leu Glu Phe Glu Lys Ile Xaa Ser Glu Gly Thr
1               5                   10                  15

Cys Leu Xaa Arg Xaa Glu Glu Glu Leu Xaa Met Xaa
            20                  25

<210> SEQ ID NO 15
```

-continued

```
<211> LENGTH: 28
<212> TYPE: PRT
<213> ORGANISM: Artificial Sequence
<220> FEATURE:
<223> OTHER INFORMATION: Made in Lab protein sequence
<220> FEATURE:
<221> NAME/KEY: MOD_RES
<222> LOCATION: (12)..(12)
<223> OTHER INFORMATION: Xaa = Arg, His or Lys
<220> FEATURE:
<221> NAME/KEY: MOD_RES
<222> LOCATION: (19)..(19)
<223> OTHER INFORMATION: Xaa = Glu or Asp
<220> FEATURE:
<221> NAME/KEY: MOD_RES
<222> LOCATION: (21)..(21)
<223> OTHER INFORMATION: Xaa = Glu or Asp
<220> FEATURE:
<221> NAME/KEY: MOD_RES
<222> LOCATION: (26)..(26)
<223> OTHER INFORMATION: Xaa = Glu or Asp
<220> FEATURE:
<221> NAME/KEY: MOD_RES
<222> LOCATION: (28)..(28)
<223> OTHER INFORMATION: Xaa = Glu or Asp

<400> SEQUENCE: 15

Arg Glu Glu Val Glu Leu Glu Phe Glu Lys Ile Xaa Ser Glu Gly Thr
1               5                   10                  15

Cys Leu Xaa Arg Xaa Glu Glu Glu Leu Xaa Met Xaa
            20                  25

<210> SEQ ID NO 16
<211> LENGTH: 225
<212> TYPE: DNA
<213> ORGANISM: Homo sapiens

<400> SEQUENCE: 16
gtaaaactgc actttgaaaa gattaagtca gaagggacct gtctgcaccg cctagaagag      60
gaactggtga tgaggaggag ggaggagctc agacacgccc tggacatcag ggagcactat     120
gaaaggaagc tggagagagc caacaacctg tatatggaac ttaatgccct catgttgcag     180
ctggaactca aggagaggga gctgctcagg cgagagcaag cttta                    225

<210> SEQ ID NO 17
<211> LENGTH: 348
<212> TYPE: DNA
<213> ORGANISM: Homo sapiens

<400> SEQUENCE: 17
ctctccacac cccaggagac ttactttaag tcccaggcag agtggcggga agaagtaaaa      60
ctgcactttg aaaagattaa gtcagaaggg acctgtctgc accgcctaga agaggaactg    120
gtgatgagga ggagggagga gctcagacac gccctggaca tcaggagca ctatgaaagg     180 aagctggaga gagccaacaa cctgtatatg gaacttaatg ccctcatgtt gcagctggaa    240
ctcaaggaga gggagctgct caggcgagag caagctttag cggaggtg cccaggcctg      300 ctgaagccac acccttcccg gggcctcctg catggaaaca caatggag                 348

<210> SEQ ID NO 18
<211> LENGTH: 348
<212> TYPE: DNA
<213> ORGANISM: Artificial Sequence
<220> FEATURE:
<223> OTHER INFORMATION: Made in Lab polynucleotide sequence

<400> SEQUENCE: 18
```

```
ctctccacac cccaggagac ttactttaag tcccaggcag agtggcggga agaagtagaa    60
ctggaatttg aaaagattaa gtcagaaggg acctgtctgc accgcctaga agaggaactg   120
gtgatgagga ggagggagga gctcagacac gccctggaca tcaggagca ctatgaaagg    180 aagctggaga gagccaacaa cctgtatatg aacttaatg ccctcatgtt gcagctggaa    240
ctcaaggaga gggagctgct caggcgagag caagctttag agcggaggtg cccaggcctg   300
ctgaagccac acccttcccg gggcctcctg catggaaaca caatggag              348
```

<210> SEQ ID NO 19
<211> LENGTH: 348
<212> TYPE: DNA
<213> ORGANISM: Artificial Sequence
<220> FEATURE:
<223> OTHER INFORMATION: Made in Lab polynucleotide sequence

<400> SEQUENCE: 19

```
ctctccacac cccaggagac ttactttaag tcccaggcag agtggcggga agaagtagaa    60
ctggaatttg aaaagattcg ttcagaaggg acctgtctgg aacgcgaaga agaggaactg   120
gaaatggaaa ggagggagga gctcagacac gccctggaca tcaggagca ctatgaaagg    180 aagctggaga gagccaacaa cctgtatatg aacttaatg ccctcatgtt gcagctggaa    240
ctccgtgaga gggagctgga aagggaagag caagctttag agcggaggtg cccaggcctg   300
ctgaagccac acccttcccg gggcctcctg catggaaaca caatggag              348
```

<210> SEQ ID NO 20
<211> LENGTH: 363
<212> TYPE: DNA
<213> ORGANISM: Artificial Sequence
<220> FEATURE:
<223> OTHER INFORMATION: Made in lab polynucleotide sequence

<400> SEQUENCE: 20

```
gccgccatgg cgctctccac accccaggag acttacttta agtcccaggc agagtggcgg    60
gaagaagtag aactggaatt tgaaaagatt cgttcagaag ggacctgtct ggaacgcgaa   120
gaagaggaac tggaaatgga aaggaggag gagctcagac acgccctgga catcaggag    180 cactatgaaa ggaagctgga gagagccaac aacctgtata tggaacttaa tgccctcatg   240
ttgcagctgg aactccgtga gggagctg aaagggaag agcaagcttt agagcggag     300 tgcccaggcc tgctgaagcc acacccttcc cggggcctcc tgcatggaaa cacaatggag   360
taa                                                               363
```

<210> SEQ ID NO 21
<211> LENGTH: 3097
<212> TYPE: DNA
<213> ORGANISM: Artificial Sequence
<220> FEATURE:
<223> OTHER INFORMATION: Made in Lab - Expression cassette
      polynucleotide sequence

<400> SEQUENCE: 21

```
cgttacataa cttacggtaa atggcccgcc tggctgaccg cccaacgacc cccgcccatt    60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacctta tgggactttc ctacttggca gtacatctac gtattagtca tcgctattac   300
```

```
catggtcgag gtgagcccca cgttctgctt cactctcccc atctccccccc cctcccacc    360
cccaattttg tatttattta ttttttaatt attttgtgca gcgatggggg cggggggggg    420
ggggggggcgg ggcgagggc ggggcggggc gaggcggaga ggtgcggcgg cagccaatca    480
gagcggcgcg ctccgaaagt ttcctttat ggcgaggcgg cggcggcggc ggccctataa    540
aaagcgaagc gcgcggcggg cgggagtcgc tgcgacgctg ccttcgcccc gtgccccgct    600
ccgccgccgc ctcgcgccgc ccgccccggc tctgactgac cgcgttactc ccacaggtga    660
gcgggcggga cggcccttct cctccgggct gtaattagcg cttggtttaa tgacggcttg    720
tttcttttct gtggctgcgt gaaagccttg aggggctccg ggaggccct ttgtgcgggg    780
ggagcggctc gggggggtgcg tgcgtgtgtg tgtgcgtggg gagcgccgcg tgcggctccg    840
cgctgcccgg cggctgtgag cgctgcgggc gcggcgcggg gctttgtgcg ctccgcagtg    900
tgcgcgaggg gagcgcggcc gggggcggtg cccgcggtg cggggggggc tgcgagggga    960
acaaaggctg cgtgcgggt gtgtgcgtgg ggggtgagc aggggtgtg ggcgcgtcgg     1020
tcgggctgca accccccctg caccccccctc cccgagttgc tgagcacggc ccggcttcgg    1080
gtgcggggct ccgtacgggg cgtggcgcgg ggctcgccgt gccggggcggg gggtggcggc    1140
aggtgggggt gccgggcggg gcggggccgc ctcgggccgg ggagggctcg ggggaggggc    1200
gcggcggccc ccgagcgcc ggcggctgtc gaggcgcggc gagccgcagc cattgccttt    1260
tatggtaatc gtgcgagagg gcgcagggac ttcctttgtc ccaaatctgt gcggagccga    1320
aatctgggag gcgccgccgc accccctcta gcgggcgcgg ggcgaagcgg tgcggcgccg    1380
gcaggaagga aatgggcggg gagggccttc gtgcgtcgcc gcgccgccgt ccccttctcc    1440
ctctccagcc tcggggctgt ccgcgggggg acggctgcct tcgggggggga cggggcaggg    1500
cggggttcgg cttctggcgt gtgaccggcg gctctagagc ctctgctaac catgttcatg    1560
ccttcttctt tttcctacag ctcctgggca acgtgctggt tattgtgctg tctcatcatt    1620
ttggcaaaga attcgagcgg ccgccagtgt gagttggacc ggtgccgcca tggcgctctc    1680
cacaccccag gagacttact ttaagtccca ggcagagtgg cgggaagaag tagaactgga    1740
atttgaaaag attcgttcag aagggacctg tctggaacgc gaagaagagg aactggaaat    1800
ggaaaggagg gaggagctca gacacgcccct ggacatcagg gagcactatg aaaggaagct    1860
ggagagagcc aacaacctgt atatggaact taatgccctc atgttgcagc tggaactccg    1920
tgagagggag ctggaagggg aagagcaagc tttagagcgg aggtgcccag gcctgctgaa    1980
gccacaccct tcccgggggcc tcctgcatgg aaacacaatg gagtaatgag gcatgcttct    2040
atattatttt ctaaaagatt taaagttttg ccttctccat ttagacttat aattcactgg    2100
aattttttttg tgtgtatggt atgacatatg ggttccctt tatttttac atataaatat    2160
atttccctgt ttttctaaaa aagacctagg aaaactgtct tcataatcaa cctctggatt    2220
acaaaatttg tgaaagattg actggtattc ttaactatgt tgctccttt acgctatgtg    2280
gatacgctgc tttaatgcct tgtatcatg ctattgcttc ccgtatggct ttcattttct    2340
cctccttgta taaatcctgg ttgctgtctc tttatgagga ttgtggccc gttgtcaggc    2400
aacgtggcgt ggtgtgcact gtgtttgctg acgcaacccc cactggttgg ggcattgcca    2460
ccacctgtca gctccttttcc gggactttcg ctttccccct ccctattgcc acggcggaac    2520
tcatcgccgc ctgccttgcc cgctgctgga caggggctcg gctgttgggc actgacaatt    2580
ccgtggtgtt gtcggggaaa tcatcgtcct ttccttggct gctcgcctat gttgccacct    2640
```

| | |
|---|---|
| ggattctgcg cgggacgtcc ttctgctacg tcccttcggc cctcaatcca gcggaccttc | 2700 |
| cttcccgcgg cctgctgccg gctctgcggc ctcttccgcg tcttcgcctt cgccctcaga | 2760 |
| cgagtcggat ctccctttgg gccgcctccc cgcatcgata ccgagcgctg ctagagagat | 2820 |
| cgatctgcct caactgtgcc ttctagttgc cagccatctg ttgtttgccc ctcccccgtg | 2880 |
| ccttccttga ccctggaagg tgccactccc actgtccttt cctaataaaa tgaggaaatt | 2940 |
| gcatcgcatt gtctgagtag gtgtcattct attctggggg gtggggtggg gcaggacagc | 3000 |
| aagggggagg attgggaaga gaatagcagg catgctgggg atgcggtggg ctctatgggt | 3060 |
| acccaggtgc tgaagaattg acccggttcc tcctggg | 3097 |

<210> SEQ ID NO 22
<211> LENGTH: 4099
<212> TYPE: DNA
<213> ORGANISM: Artificial Sequence
<220> FEATURE:
<223> OTHER INFORMATION: Made in Lav - Expression cassette
      polynucleotide sequence

<400> SEQUENCE: 22

| | |
|---|---|
| atgtcctaca gcgcgctcgc tcgctcactg aggccgcccg ggcaaagccc gggcgtcggg | 60 |
| cgacctttgg tcgcccggcc tcagtgagcg agcgagcgcg cagagaggga gtggccaact | 120 |
| ccatcactag gggttccttg tagttaatga ttaacctctg gagaccgcca tgctacttat | 180 |
| ctaccagggt aatgggatcc tctagaaact atagcgttac ataacttacg gtaaatggcc | 240 |
| cgcctggctg accgcccaac gacccccgcc cattgacgtc aataatgacg tatgttccca | 300 |
| tagtaacgcc aatagggact tccattgacg tcaatgggtg gagtattta cggtaaactg | 360 |
| cccacttggc agtacatcaa gtgtatcata tgccaagtac gccccctatt gacgtcaatg | 420 |
| acggtaaatg gcccgcctgg cattatgccc agtacatgac cttatgggac tttcctactt | 480 |
| ggcagtacat ctacgtatta gtcatcgcta ttaccatggt cgaggtgagc ccacgttct | 540 |
| gcttcactct ccccatctcc cccccctccc cacccccaat tttgtattta tttattttt | 600 |
| aattatttg tgcagcgatg ggggcggggg ggggggggg gcgggcgag gggcggggcg | 660 |
| gggcgaggcg gagaggtgcg gcggcagcca atcagagcgg cgcgctccga aagtttcctt | 720 |
| ttatggcgag gcggcggcgg cggcggccct ataaaaagcg aagcgcgcgg cgggcgggag | 780 |
| tcgctgcgac gctgccttcg ccccgtgccc cgctccgccg ccgcctcgcg ccgcccgccc | 840 |
| cggctctgac tgaccgcgtt actcccacag gtgagcgggc gggacggccc ttctcctccg | 900 |
| ggctgtaatt agcgcttggt ttaatgacgg cttgtttctt ttctgtggct gcgtgaaagc | 960 |
| cttgagggc tccggagggc ccctttgtgc gggggagcg gctcggggg tgcgtgcgtg | 1020 |
| tgtgtgtgcg tggggagcgc gcgtgcggc tccgcgctgc ccggcggctg tgagcgctgc | 1080 |
| gggcgcggcg cggggctttg tgcgctccgc agtgtgcgcg aggggagcgc ggccgggggc | 1140 |
| ggtgccccgc ggtgcggggg gggctgcgag gggaacaaag gctgcgtgcg gggtgtgtgc | 1200 |
| gtggggggt gagcaggggg tgtgggcgcg tcggtcgggc tgcaaccccc cctgcacccc | 1260 |
| cctccccgag ttgctgagca cggcccggct tcgggtgcgg ggctccgtac ggggcgtggc | 1320 |
| gcggggctcg ccgtgccggg cgggggtgg cggcaggtgg gggtgccggg cggggcgggg | 1380 |
| ccgcctcggg ccggggaggg ctcgggggag gggcgcggcg gccccggag cgccggcggc | 1440 |
| tgtcgaggcg cggcgagccg cagccattgc cttttatggt aatcgtgcga gagggcgcag | 1500 |
| ggacttcctt tgtcccaaat ctgtgcggag ccgaaatctg ggaggcgccg ccgcacccc | 1560 |

-continued

```
tctagcgggc gcggggcgaa gcggtgcggc gccggcagga aggaaatggg cggggagggc    1620
cttcgtgcgt cgccgcgccg ccgtccccct ctccctctcc agcctcgggg ctgtccgcgg    1680
ggggacggct gccttcgggg gggacggggc agggcggggt tcggcttctg cgtgtgacc     1740
ggcggctcta gagcctctgc taaccatgtt catgccttct tcttttttcct acagctcctg   1800
ggcaacgtgc tggttattgt gctgtctcat cattttggca aagaattcga gcggccgcca    1860
gtgtgagttg gaccggtgcc gccatggcgc tctccacacc ccaggagact tactttaagt    1920
cccaggcaga gtggcgggaa gaagtagaac tggaatttga aaagattcgt tcagaaggga    1980
cctgtctgga acgcgaagaa gaggaactgg aaatggaaag gagggaggag ctcagacacg    2040
ccctggacat cagggagcac tatgaaagga agctggagag agccaacaac ctgtatatgg    2100
aacttaatgc cctcatgttg cagctggaac tccgtgagag ggagctggaa agggaagagc    2160
aagctttaga gcggaggtgc ccaggcctgc tgaagccaca cccttcccgg ggcctcctgc    2220
atggaaacac aatggagtaa tgaggcatgc ttctatatta ttttctaaaa gatttaaagt    2280
tttgccttct ccatttagac ttataattca ctggaatttt tttgtgtgta tggtatgaca    2340
tatgggttcc cttttatttt ttacatataa atatatttcc ctgttttcct aaaaaagacc    2400
taggaaaact gtcttcataa tcaacctctg gattacaaaa tttgtgaaag attgactggt    2460
attcttaact atgttgctcc ttttacgcta tgtggatacg ctgctttaat gcctttgtat    2520
catgctattg cttcccgtat ggctttcatt ttctcctcct tgtataaatc ctggttgctg    2580
tctctttatg aggagttgtg gcccgttgtc aggcaacgtg gcgtggtgtg cactgtgttt    2640
gctgacgcaa cccccactgg ttggggcatt gccaccacct gtcagctcct ttccgggact    2700
ttcgctttcc cctccctat tgccacggcg gaactcatcg ccgcctgcct tgcccgctgc     2760
tggacagggg ctcggctgtt gggcactgac aattccgtgg tgttgtcggg gaaatcatcg    2820
tcctttcctt ggctgctcgc ctatgttgcc acctggattc tgcgcgggac gtccttctgc    2880
tacgtcccct cggccctcaa tccagcggac cttccttccc gcggcctgct gccggctctg    2940
cggcctcttc cgcgtcttcg ccttcgccct cagacgagtc ggatctccct ttgggccgcc    3000
tccccgcatc gataccgagc gctgctagag agatcgatct gcctcaactg tgccttctag    3060
ttgccagcca tctgttgttt gcccctcccc cgtgccttcc ttgaccctgg aaggtgccac    3120
tcccactgtc ctttcctaat aaaatgagga aattgcatcg cattgtctga gtaggtgtca    3180
ttctattctg gggggtgggg tggggcagga cagcaagggg gaggattggg aagagaatag    3240
caggcatgct ggggatgcgg tgggctctat gggtacccag gtgctgaaga attgacccgg    3300
ttcctcctgg ggaagcaatt cgttgatctg aatttcgacc accgataata cctattaccc    3360
tggtagataa gtagcacggc gggttaatga ttaactacag caattcgttg atctgaattt    3420
cgaccaccca taatagatct cccattaccc tggtagataa gtagcatggc gggacaatta    3480
agtacctcaa agaactattc ttgtttgcct tattcctatg taaataactg aaatctttgt    3540
ttttcttcct aaaagggggtg atgttgattt ttacttacaa tgtatttaa gtttgtcact    3600
ctaaatggtt atgagcaagt ttaagaaaaa tcttcagcaa atactacctt agattatgac    3660
cccaaaacac atttacttat gattatgttg aaaacatagg gtctgggaa aaagggattt     3720
aaattaagaa gaaaaagaag acttcggact taaaaagtct tttagaggcc agctcaccaa    3780
caacacaaca ccgagtctgt gttgcacaat atgttactta ggtataaatc aaggattcat    3840
gtaattttgt cattccttgc gtgatatttt aaaaaacatt ctgtgtaagg tatttataaa    3900
gctctcttct aaaaatacaa aaatttgtgt cattaatcaa cagtcaggtt aatcattaac    3960
```

-continued

```
tacaaggaac ccctagtgat ggagttggcc actccctctc tgcgcgctcg ctcgctcact      4020
gaggccgggc gaccaaaggt cgcccgacgc ccgggctttg cccgggcggc ctcagtgagc      4080
gagcgagcgc gcactgtca                                                   4099

<210> SEQ ID NO 23
<211> LENGTH: 89
<212> TYPE: RNA
<213> ORGANISM: Homo sapiens

<400> SEQUENCE: 23
ugcugcuggc cagagcucuu uucacauugu gcuacugucu gcaccuguca cuagcagugc      60
aauguuaaaa gggcauuggc cguguagug                                        89

<210> SEQ ID NO 24
<211> LENGTH: 23
<212> TYPE: RNA
<213> ORGANISM: Homo sapiens

<400> SEQUENCE: 24
uacccuguag auccgaauuu gug                                              23

<210> SEQ ID NO 25
<211> LENGTH: 24
<212> TYPE: RNA
<213> ORGANISM: Homo sapiens

<400> SEQUENCE: 25
uuaaugcuaa ucgugauagg gguu                                             24

<210> SEQ ID NO 26
<211> LENGTH: 71
<212> TYPE: RNA
<213> ORGANISM: Homo sapiens

<400> SEQUENCE: 26
gcgacuguaa acauccucga cuggaagcug ugaagccaca gaugggcuuu cagucggaug      60
uuugcagcug c                                                           71
```

UNITED STATES PATENT AND TRADEMARK OFFICE
CERTIFICATE OF CORRECTION

Page 1 of 1

PATENT NO. : 12,270,033 B2
APPLICATION NO. : 17/430269
DATED : April 8, 2025
INVENTOR(S) : Thomas W. Chalberg, Jr.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 792 days.

Signed and Sealed this
Twelfth Day of August, 2025

Coke Morgan Stewart
*Acting Director of the United States Patent and Trademark Office*